US011996006B2

(12) United States Patent
Betteridge et al.

(10) Patent No.: US 11,996,006 B2
(45) Date of Patent: May 28, 2024

(54) VIRTUAL REALITY PLATFORM FOR TRAINING MEDICAL PERSONNEL TO DIAGNOSE PATIENTS

(71) Applicant: VxMED, LLC, Lubbock, TX (US)

(72) Inventors: Anthony Betteridge, Lubbock, TX (US); Nathan Lloyd, Lubbock, TX (US); Jordan Ketring, Lubbock, TX (US)

(73) Assignee: VxMED, LLC, Lubbock, TX (US)

( * ) Notice: Subject to any disclaimer, the term of this patent is extended or adjusted under 35 U.S.C. 154(b) by 715 days.

(21) Appl. No.: 17/221,579

(22) Filed: Apr. 2, 2021

(65) Prior Publication Data
US 2021/0312833 A1    Oct. 7, 2021

Related U.S. Application Data

(60) Provisional application No. 63/005,430, filed on Apr. 5, 2020.

(51) Int. Cl.
*G09B 23/28*     (2006.01)
*G06T 7/00*      (2017.01)
(Continued)

(52) U.S. Cl.
CPC ............ *G09B 23/28* (2013.01); *G06T 7/0012* (2013.01); *G06T 19/006* (2013.01); *G09B 5/06* (2013.01);
(Continued)

(58) Field of Classification Search
CPC .......... G09B 23/28; G09B 5/06; G16H 10/60; G16H 50/20; G06T 7/0012; G06T 19/006; G06T 2219/024
See application file for complete search history.

(56) References Cited

U.S. PATENT DOCUMENTS

2005/0255434 A1    11/2005    Lok et al.
2015/0221236 A1    8/2015     Forte et al.
(Continued)

OTHER PUBLICATIONS

Buche et al, "Mascaret: Pedagogical Multi-agents System for Virtual Environment for Training," Journal of Distance Education Technologies, 2004. Retrieved on Apr. 29, 2021 from <URL: https://hal.archives-ouvertes.fr/hal-00610857/document>.
(Continued)

*Primary Examiner* — Timothy A Musselman
(74) *Attorney, Agent, or Firm* — Kirton McConkie; Brian Tucker

(57) ABSTRACT

A virtual reality platform is provided for training medical personnel to diagnose patients. A virtual reality platform can include application software that creates a virtual reality environment in which patients having a variety of conditions can be examined. As the user interacts with a patient in the virtual reality environment, the application software can present elements of patient information. The application software can track whether the user discovers the elements of patient information that are necessary to arrive at the correct diagnosis for the correct reasons and present a corresponding score to assist the user in developing his or her diagnosing skills. The application software may also be configured to provide a differential diagnose coach feature to enable the user to learn how each element of patient information he or she discovers when examining a patient may impact the likelihood that the patient has a particular condition.

19 Claims, 20 Drawing Sheets

(51) Int. Cl.
  *G06T 19/00* (2011.01)
  *G09B 5/06* (2006.01)
  *G16H 10/60* (2018.01)
  *G16H 50/20* (2018.01)

(52) U.S. Cl.
  CPC ............ *G16H 10/60* (2018.01); *G16H 50/20* (2018.01); *G06T 2219/024* (2013.01)

(56) References Cited

U.S. PATENT DOCUMENTS

| | | |
|---|---|---|
| 2015/0279238 A1* | 10/2015 | Forte ................. G09B 23/28 434/271 |
| 2015/0287330 A1 | 10/2015 | Kron et al. |
| 2016/0328998 A1 | 11/2016 | Pedersen et al. |
| 2020/0286294 A1* | 9/2020 | Musara ................. G16H 50/30 |

OTHER PUBLICATIONS

Dunne et al, "Pulse!!: A Model for Research and Development of Virtual-Reality Learning in Military Medical Education and Training," Military Medicine, vol. 175, Issue Suppl_7, Jul. 2010, pp. 25-27. Retreived on May 29, 2021 from <URL: https://academic.oup.com/milmed/article/175/suppl_7/25/4344641?login=true>.

* cited by examiner

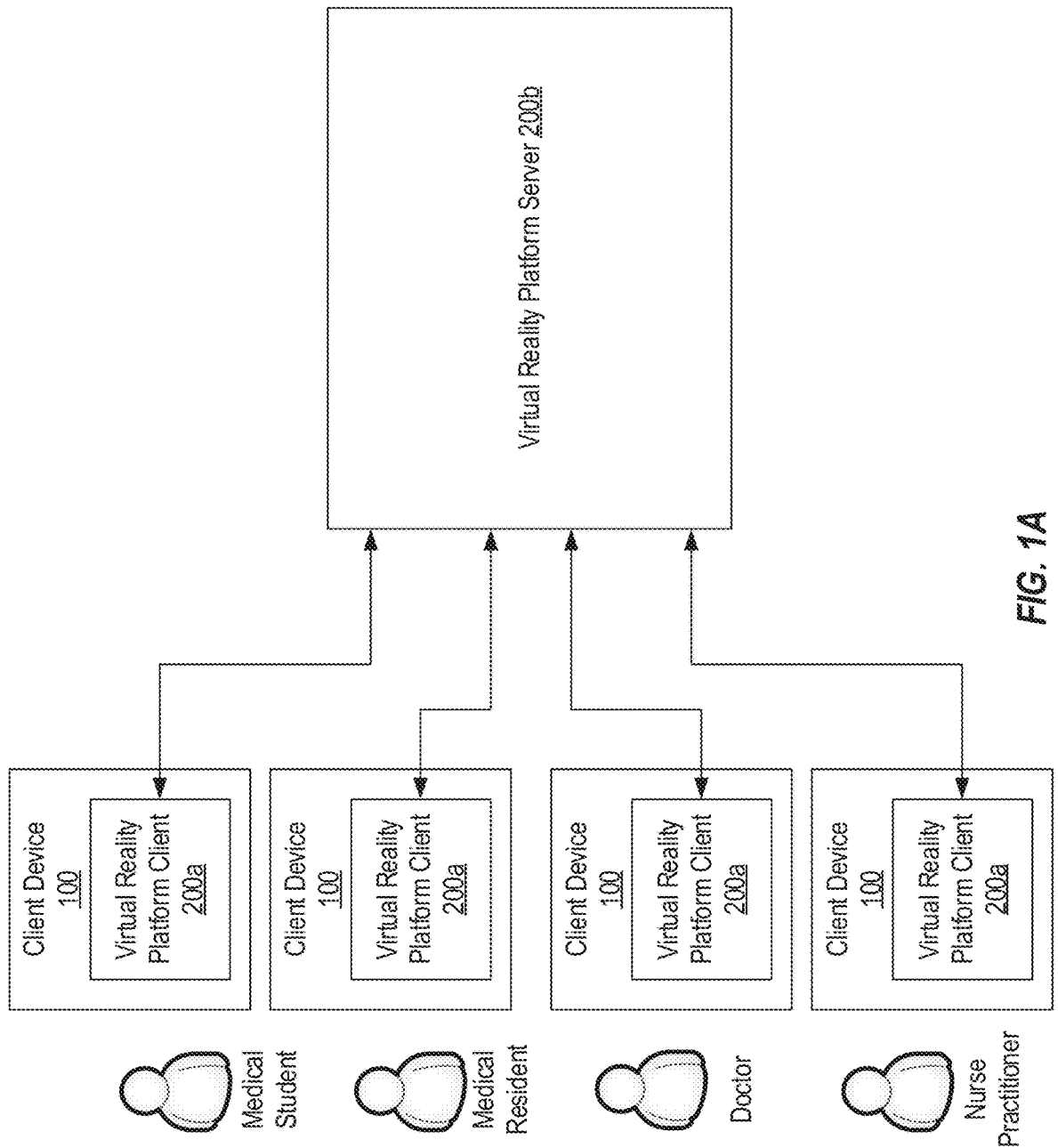

Feedback on Essential Tests

You failed to order an electrocardiogram (ekg)

You failed to order a radiography

You failed to order a cardiac enzymes.

You failed to perform the abdominal physical exam.

You failed to perform the musculoskeletal physical exam.

Differential Diagnosis Data Structures 500

Prevalence/Incidence Data Structure 501

| Condition | Prevalence/Incidence |
|---|---|
| ST Segment Elev… | 1% |
| Non ST Segment Elev… | 1% |
| Unstable Angina | 1% |
| … | |

Diagnosis Likelihood Data Structure 502

| Condition | Likelihood |
|---|---|
| ST Segment Elev… | 1% |
| Non ST Segment Elev… | 1% |
| Unstable Angina | 1% |
| … | |

Likelihood Ratio Data Structure 503

| Condition | Element 1 Likelihood Ratio | Element 2 Likelihood Ratio | Element 3 Likelihood Ratio | Element 4 Likelihood Ratio |
|---|---|---|---|---|
| ST Segment Elev… | 1.2 | 2 | 0.8 | 1 |
| Non ST Segment Elev… | 1.2 | 1 | 0.7 | 1 |
| Unstable Angina | 1.2 | 1 | 0.1 | 1 |
| … | … | … | … | … |

*FIG. 6*

VIRTUAL REALITY PLATFORM FOR TRAINING MEDICAL PERSONNEL TO DIAGNOSE PATIENTS

CROSS-REFERENCE TO RELATED APPLICATIONS

This application claims priority to U.S. Provisional Patent Application No. 63/005,430, which was filed on Apr. 5, 2020 and which is incorporated by reference.

BACKGROUND

A common issue with high level practice is experience. Exposure to every day practice of any profession creates a gap between the novice and the expert. Novices can only become experts through experience, but this experience can be intimidating and difficult at best, and often can be associated with a painful learning process. In the medical field, this can potentially mean a lower quality of care for a patient.

One particular field where experience is necessary to improve one's skills in the art is the medical field. Medical professionals are subjected to complex tasks involving an overlapping of a variety of complex human systems. Combine these systems with historical patient data, environmental effects, and more, and it quickly becomes apparent how complex any single task can be for a medical professional. Inexperienced medical professionals or learning medical professionals may have difficulty digesting all this information while also learning. Even experienced practitioners are often victims of their own subjective analysis.

To complicate matters further, due to the complexity of tasks associated with the medical profession, it has been impossible to develop an objective means to measure the success of such tasks. Many tasks are determined to be successful if they help a patient feel better or improve upon the lives of a patient. Micro-data or large scale objective data is almost impossible to come by. Furthermore, large scale ratings or ratings for success of a student in harnessing these skills is impossible to measure.

Current academic training methods for the medical profession, and particularly for the art of making a diagnosis of a patient are very difficult for students to learn and may be even more difficult to teach. Furthermore, evaluating how well a student has learned this art may be inaccurate which results in a poor evaluation of the student's abilities. Having a true measure of one's abilities is critical to awarding a student for his or her accomplishments. Thus, a means of improving teaching, evaluation, and diagnosing is severely needed in the art of both teaching and practicing.

So, while there are teaching methods currently being used in the art which consist of in class instruction, video instruction, and textbook study, these common methods may not be considered real world. Furthermore, these learning methods do not provide a medical professional with what the actual practice of medicine will look like.

Complicating matters further, diagnostic procedures used in the medical profession are complex tasks that include many variables and factors which are patient dependent. Textbooks are not able to simulate a variety of these various factors in a simulation. Thus, learning the diagnostic process in the medical profession is extremely difficult for students and teachers in a classroom setting. For this reason, it usually takes practice, sometimes years of practice, to harness the skill of diagnosis. This involves treating hundreds of patients and oftentimes not having any feedback, or only having the feedback of patients. In some cases, it may be that a physician never fully developed an effective diagnostic method.

BRIEF SUMMARY

Embodiments of the present invention extend to systems, method and computer program products for implementing a virtual reality platform for training medical personnel to diagnose patients. A virtual reality platform can include application software that creates a virtual reality environment in which patients having a variety of conditions can be examined. As the user interacts with a patient in the virtual reality environment, the application software can present elements of patient information. The application software can track whether the user discovers the elements of patient information that are necessary to arrive at the correct diagnosis for the correct reasons and present a corresponding score to assist the user in developing his or her diagnosing skills. The application software may also be configured to provide a differential diagnose coach feature to enable the user to learn how each element of patient information he or she discovers when examining a patient may impact the likelihood that the patient has a particular condition.

In some embodiments, the present invention may be implemented by a virtual reality platform that includes application software as a method for providing a virtual reality environment for training medical personnel to diagnose patients. The application software can generate a virtual reality environment that includes a patient. The patient can be associated with patient information that represents a first condition that the patient has out of a plurality of possible conditions. The application software can detect a first user interaction with the virtual reality environment. The first user interaction may identify a first examination or diagnostics procedure that a user desires to perform on the patient in the virtual reality environment. In response to detecting the first user interaction, the application software can access the patient information to retrieve one or more elements of the patient information that correspond with the first examination or diagnostics procedure. The application software can present, in the virtual reality environment, the one or more elements of the patient information that correspond with the first examination or diagnostics procedure. In conjunction with presenting the one or more elements of the patient information that correspond with the first examination or diagnostics procedure, the application software can adjust a score that is based on which elements of the patient information the user has discovered by interacting with the virtual reality environment.

In some embodiments, the present invention may be implemented as computer storage media storing computer executable instructions which when executed implement application software of a virtual reality platform. The application software may be configured to perform a method for providing a virtual reality environment for training medical personnel to diagnose patients. The application software can generate a virtual reality environment that includes a patient. The patient can be associated with patient information that represents a first condition that the patient has out of a plurality of possible conditions. The application software can present a differential diagnosis coach overlay in the virtual reality environment. The differential diagnosis coach overlay may identify a first plurality of conditions of the plurality of possible conditions and a likelihood value for each of the first plurality of conditions. The application software can detect a first user interaction with the virtual reality environment. The first user interaction may identify a first examination or diagnostics procedure that a user desires to perform on the patient in the virtual reality environment. In response to detecting the first user interaction, the application software can access the patient information to retrieve one or more elements of the patient information that correspond with the first examination or diagnostics procedure. In conjunction with accessing the patient information to retrieve the one or more elements of the patient information that correspond with the first examination or diagnostics procedure, the application software can adjust the likelihood value for at least one of the first plurality of conditions. After adjusting the likelihood value for at least one of the first plurality of conditions, the application software can adjust the first plurality of conditions that are identified in the differential diagnosis coach overlay.

In some embodiments, the present invention may be implemented by application software of a virtual reality platform as a method for providing a virtual reality environment for training medical personnel to diagnose patients. The application software can generate a virtual reality environment that includes a patient. The patient can be associated with patient information that represents a first condition that the patient has out of a plurality of possible conditions. The application software can detect a first user interaction with the virtual reality environment. The first user interaction may identify a first examination that a user desires to perform on the patient in the virtual reality environment. In response to detecting the first user interaction, the application software can access the patient information to retrieve one or more elements of examination information that correspond with the first examination. The application software can present, in the virtual reality environment, the one or more elements of the examination information that correspond with the first examination. The application software can detect a second user interaction with the virtual reality environment. The second user interaction may identify a first diagnostics procedure that the user desires to perform on the patient in the virtual reality environment. In response to detecting the second user interaction, the application software may access the patient information to retrieve one or more elements of diagnostics information that correspond with the first diagnostics procedure. The application software can present, in the virtual reality environment, the one or more elements of the diagnostics information that correspond with the first diagnostics procedure. The application software can maintain a differential diagnostics coach overlay within the virtual reality environment. The differential diagnosis coach overlay can identify a first plurality of conditions of the plurality of possible conditions and a likelihood value for each of the first plurality of conditions. Maintaining the different diagnostics coach overlay can include adjusting the likelihood values for at least some of the first plurality of conditions in response to presenting the one or more elements of the examination information and the one or more elements of diagnostics information.

BRIEF DESCRIPTION OF THE DRAWINGS

Understanding that these drawings depict only typical embodiments of the invention and are not therefore to be considered limiting of its scope, the invention will be described and explained with additional specificity and detail through the use of the accompanying drawings in which:

FIGS. 1A and 1B each provide an example computing environment in which a virtual reality platform for training medical personnel to diagnose patients may be implemented;

FIGS. 3A-3F provide examples of a virtual reality environment that the virtual reality platform may generate in some embodiments;

FIG. 6 provides an example of various differential diagnosis data structures that the differential diagnosis coach module may use.

DETAILED DESCRIPTION

Figure 1B:
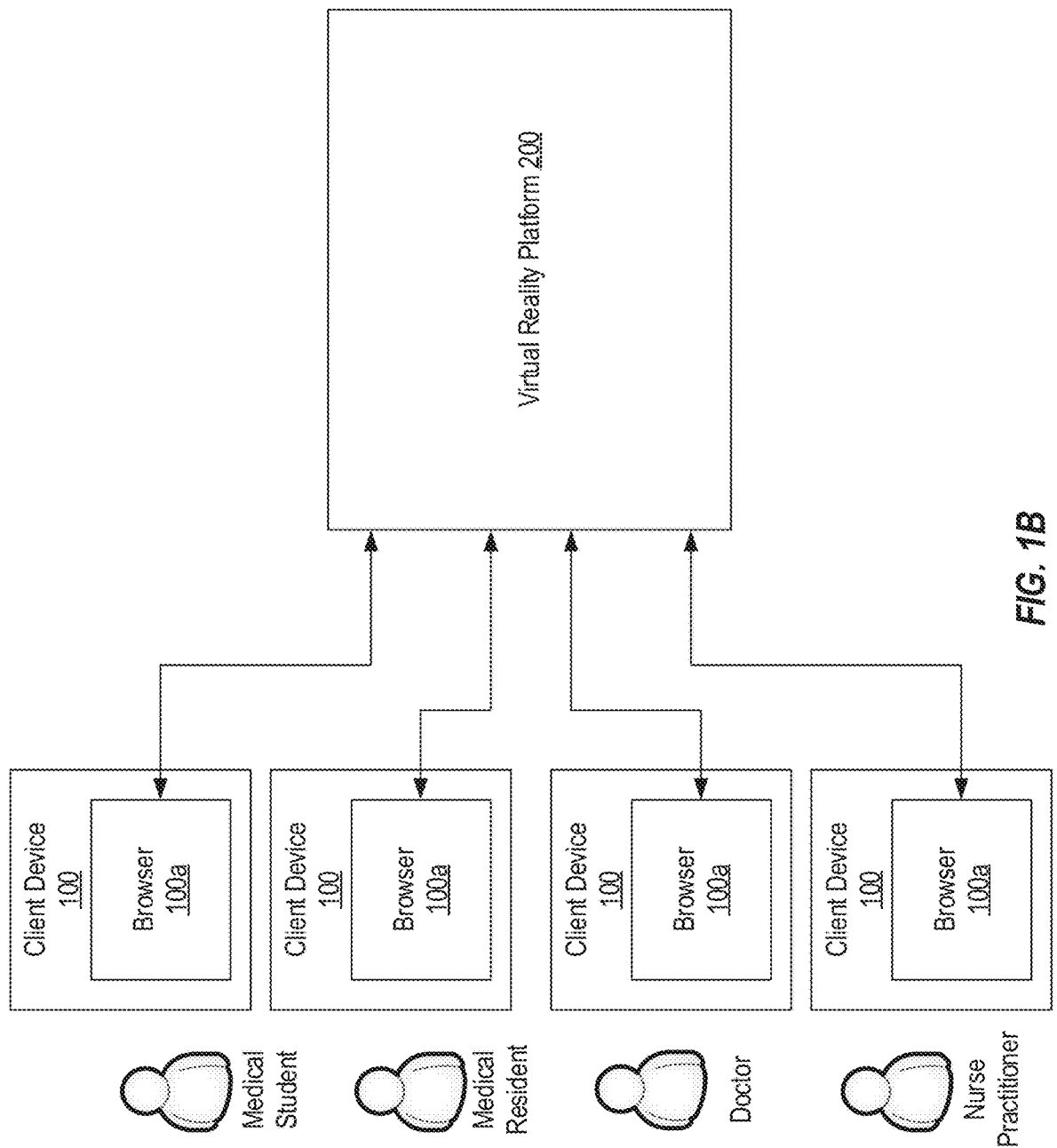

FIG. 1A illustrates an example computing environment in which embodiments of the present invention may be implemented. As shown, the example computing environment includes any number of client devices 100 and a virtual reality platform 200. Client devices 100 can represent any end-user computing device such as a desktop, laptop, smart phone, smart television, virtual reality headset, gaming system, etc. In this example embodiment, virtual reality platform 200 is implemented as a virtual reality platform client 200a that is installed locally on client device 100 (e.g., as a desktop or mobile application) and a virtual reality platform server(s) 200b with which each virtual reality platform client 200a interfaces. However, as represented by FIG. 1B, in some embodiments, virtual reality platform 200 may be entirely web-based and therefore accessible via a browser 100a on client device 100. Although not depicted in the figures, in some embodiments, virtual reality platform 200 may be entirely implemented on client device 100. Accordingly, embodiments of the present invention should not be limited to any particular environment or architecture that may be used to implement virtual reality platform 200.

In the specification, virtual reality platform 200 will be described as being configured to train medical personnel to diagnose patients. Accordingly, FIGS. 1A and 1B show, as examples, a medical student, a medical resident, a doctor and a nurse practitioner (collectively "medical personnel" or "users") employing client devices 100 to access virtual reality platform 200. It should be understood, however, that virtual reality platform 200 could be used in other contexts such as by dentists, veterinarians or other personnel that perform medical diagnoses on living organisms.

Figure 2:
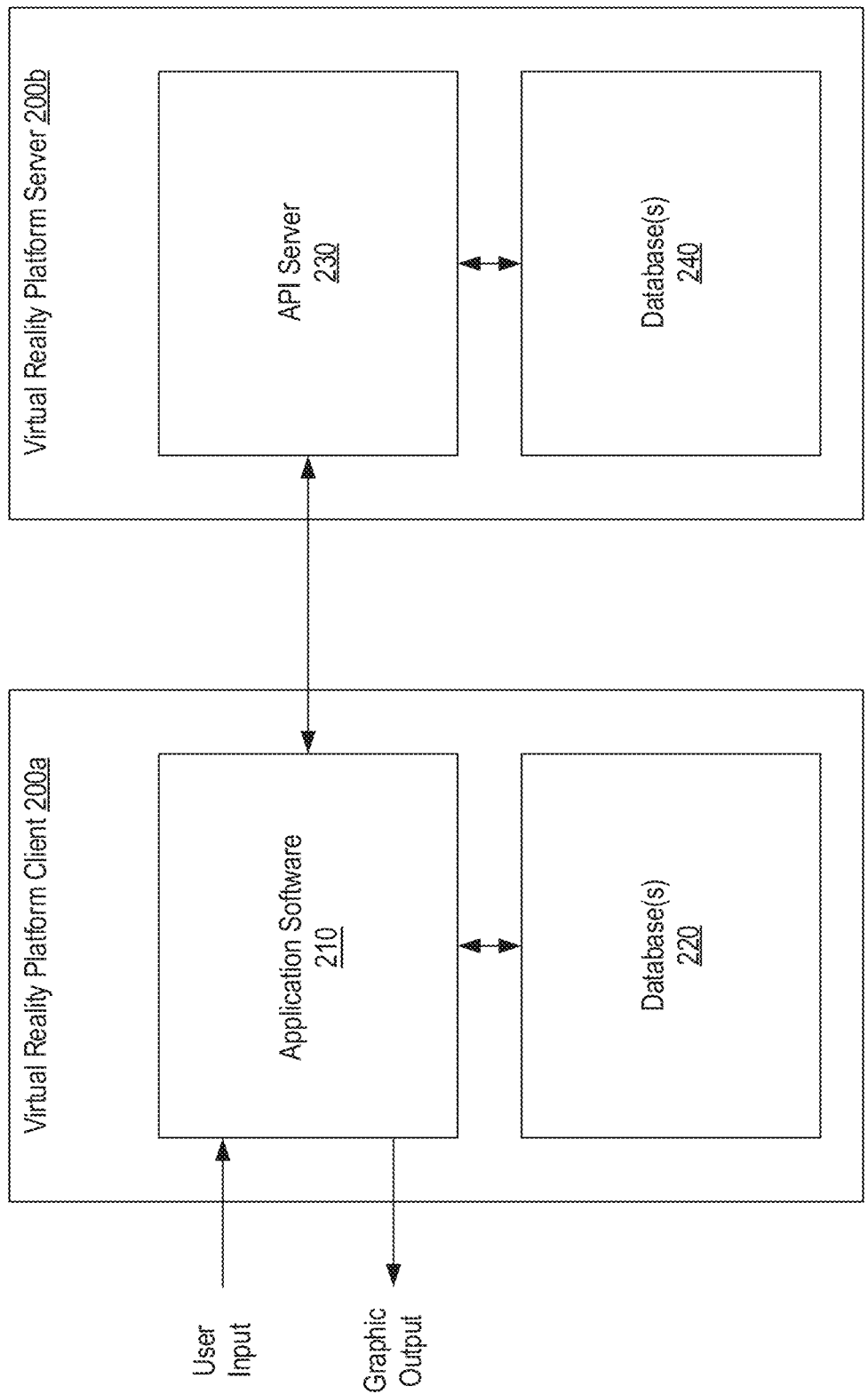
FIG. 2 provides an example of various components that may be used in some embodiments to implement a virtual reality platform for training medical personnel to diagnose patients.

FIG. 2 provides an example of various components that virtual reality platform 200 may include in some embodiments of the present invention. For this example, it will be assumed that virtual reality platform 200 employs a client/server model and therefore includes virtual reality platform client 200a and virtual reality platform server 200b. Virtual reality platform client 200a can include application software 210 and one or more databases 220, whereas virtual reality platform server 200b can include an API server 230 and one or more databases 240. In this context, the term "database" should be construed as encompassing any data storage structure or technique.

Application software 210 can represent the executable components that create a virtual reality environment on client device 100. Accordingly, application software 210 can generate graphic output constituting the virtual reality environment and output it for display on/by client device 100. Application software 210 can also receive user input directed to the virtual reality environment and may process such user input to update the virtual reality environment. Application software 210 can also employ such user input to train the user as described below.

Figure 2A:
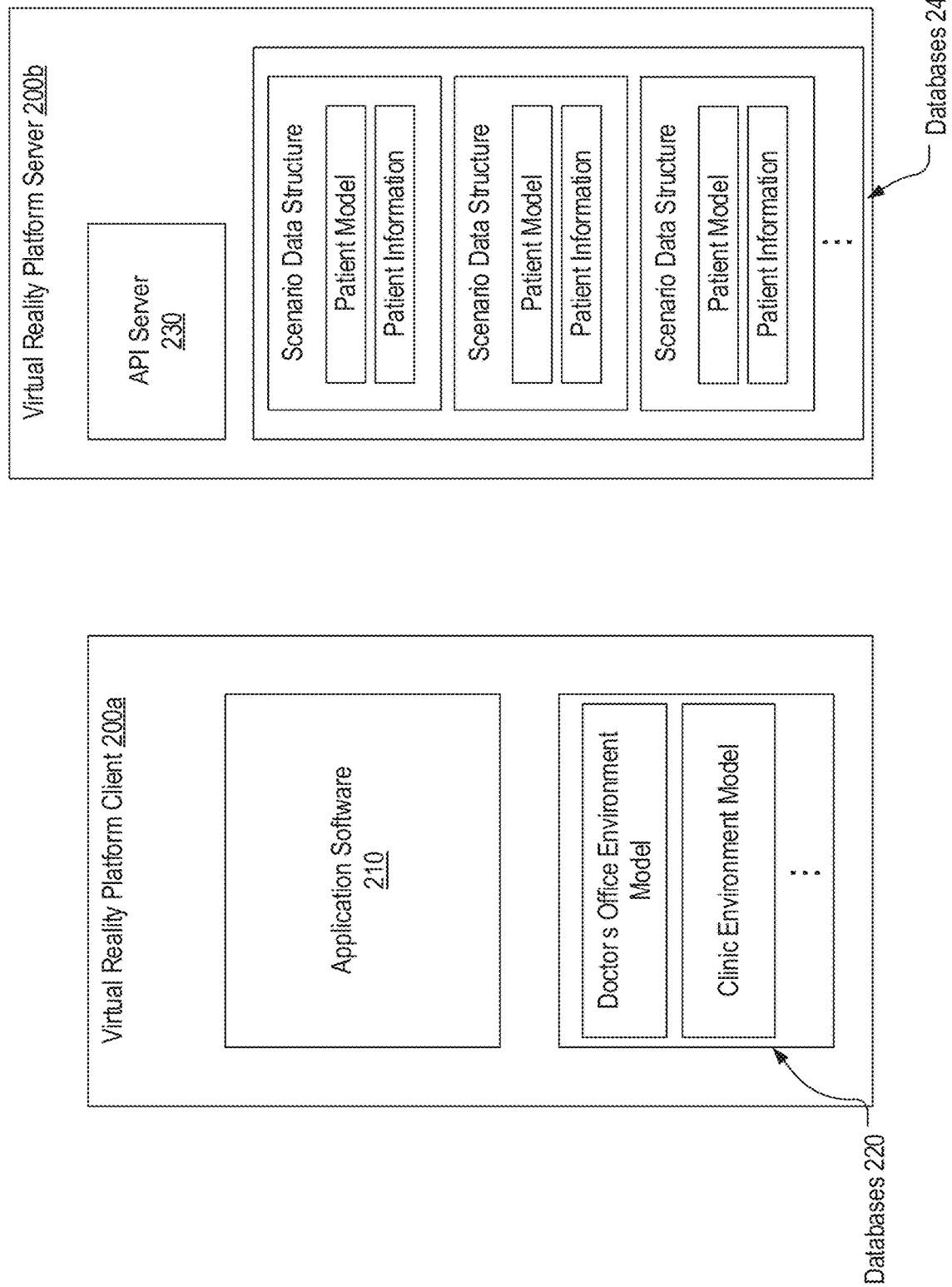
FIG. 2A provides an example of various data structures that may be used in some embodiments to implement a virtual reality platform for training medical personnel to diagnose patients.

Databases 220 can store any data or content that application software 210 may employ to create and manipulate the virtual reality environment. For example, databases 220 may store a model for rendering the virtual reality environment such as in the form of a doctor's office or clinic as is represented in FIG. 2A.

API Server 230 can represent one or more services that receive and respond to requests from instances of application software 210 running on client devices 100. API server 230 may respond to such requests by retrieving various types of content or data from databases 240. For example, API server 230 can allow application software 210 to request scenario data structures which represent scenarios that can be generated in the virtual reality environment. In this context, a scenario can be viewed as a virtual representation of a patient who has a particular condition or conditions that can be diagnosed. A scenario data structure may therefore include a model (or a reference to a model) for rendering a representation of the patient within the virtual reality environment and data defining characteristics of and/or information about the patient such as the patient's history (e.g., medical, surgical, family, sexual, social, etc.), current symptoms, current medications, current complaints, diagnostic results, etc. (hereinafter "patient information"). As one specific example, a scenario data structure representing a scenario where a patient is having a heart attack (i.e., an ST-segment elevation myocardial infarction) may include patient information consisting of vitals, characteristics, conditions, diagnostic results, etc. representative of what would be expected when an actual patient has a heart attack.

Figure 3A:
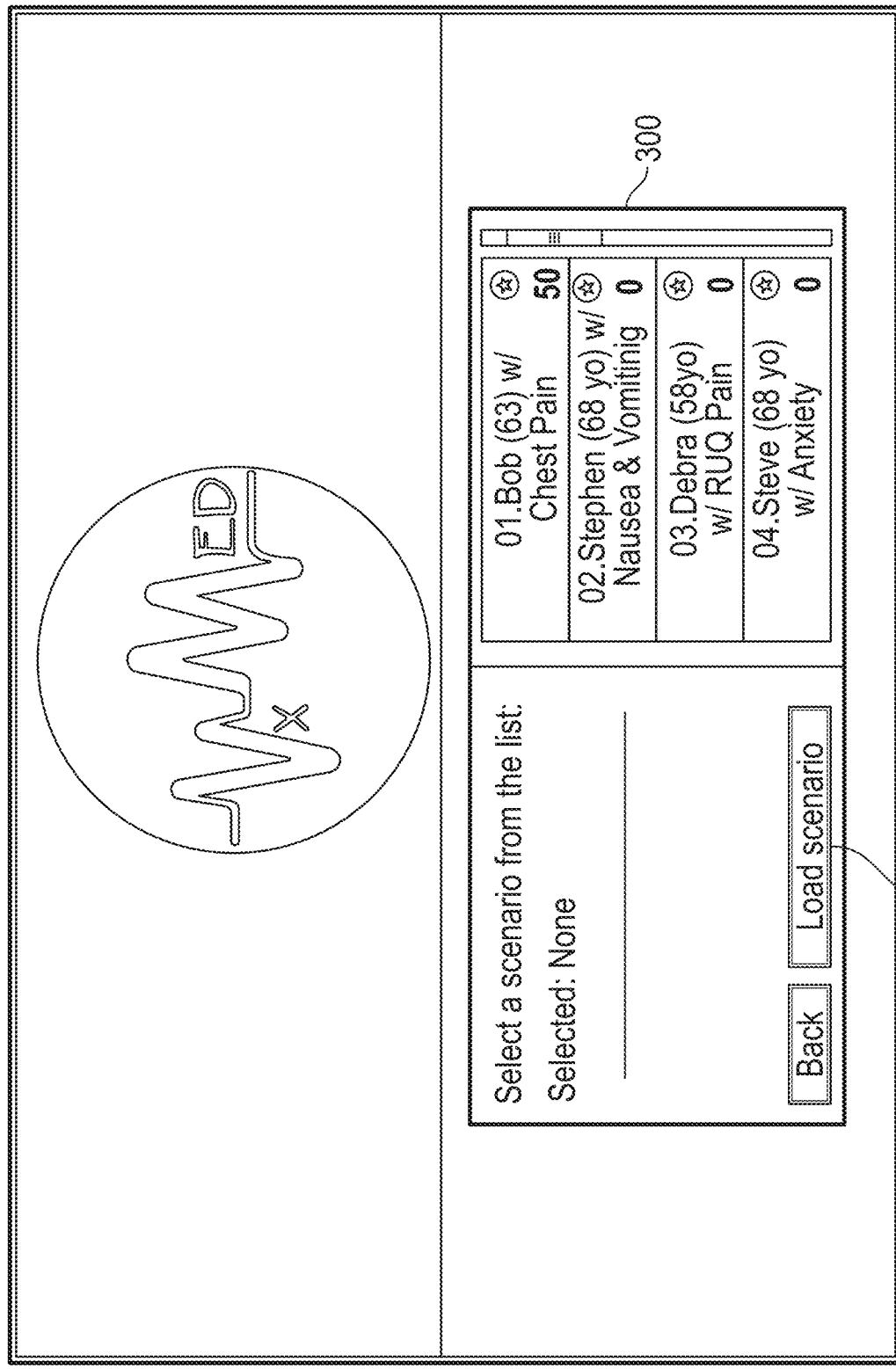

FIGS. 3A-3E provide an example of how application software 210 can generate a virtual reality environment to enable medical personnel to diagnose virtual patients. FIG. 3A provides an example of a user interface that application software 210 can generate based on scenario data structures it receives to allow the user to select a scenario to be rendered in the virtual reality environment. As shown, the user interface can include a list 300 of scenarios that are available and button 301 for loading a particular scenario. List 300 can include a brief description of the available scenarios. For example, the first scenario in list 300 represents a patient named Bob who is 63 and is experiencing chest pain. Application software 210 can obtain such content describing the scenario from the scenario data structures it may retrieve via API server 230.

Figure 3B:
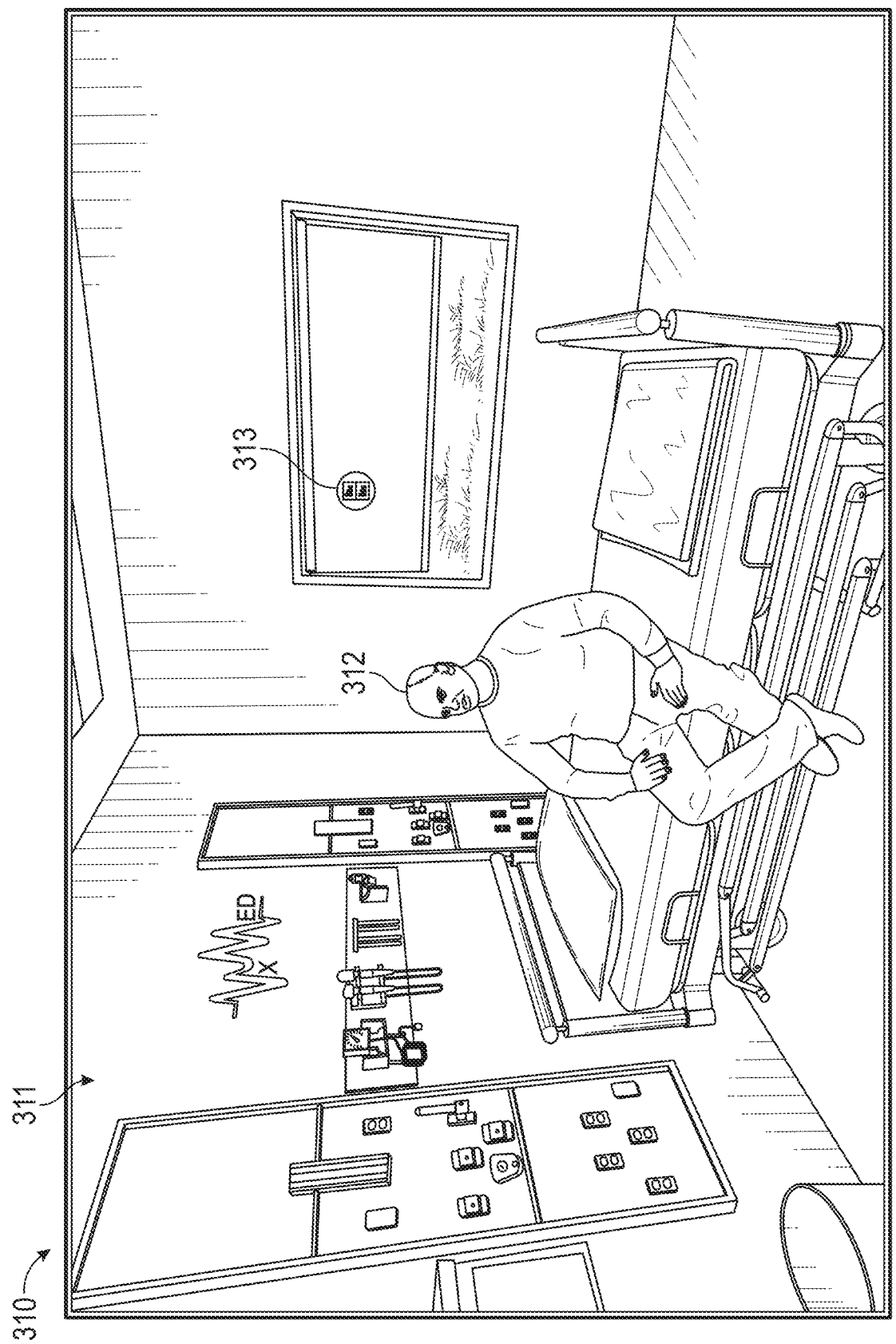

FIG. 3B provides an example of a virtual reality environment 310 that application software 210 may generate when the user selects a particular scenario. For example, if the user selected the first scenario in list 300 and selected button 301, application software 210 could retrieve the model representing a doctor's office and the patient model from (or referenced by) the selected scenario data structure to render virtual reality environment 310. Virtual reality environment 310 can include a visual representation 311 of a doctor's office, clinic or any other setting that may be defined in a model and a visual representation 312 of the patient as defined in the patient model. Application software 210 can also render virtual reality environment 310 to include a selectable component 313 that the user can select to commence a process of diagnosing the patient. Application software 210 may allow the user to navigate within and interact with virtual reality environment 310 using any input controls available on client device 100.

Figure 3C:

FIG. 3C provides an example of how application software 210 may update virtual reality environment 310 in response to the user selecting selectable component 313 to commence diagnosing the patient. As shown, application software 210 may retrieve the patient history of the patient information from the selected scenario data structure and present it in a history overlay 320 that is presented overtop virtual reality environment 310. History overlay 320 allows the user to review the patient history for the particular scenario prior to commencing a virtual examination. History overlay 320 may include a button 321 that the user can select to proceed to the virtual examination. As described in detail below, application software 210 may also generate a differential diagnosis coach overlay 330 which includes a list 331 of potential diagnoses (or conditions).

Figure 3D:
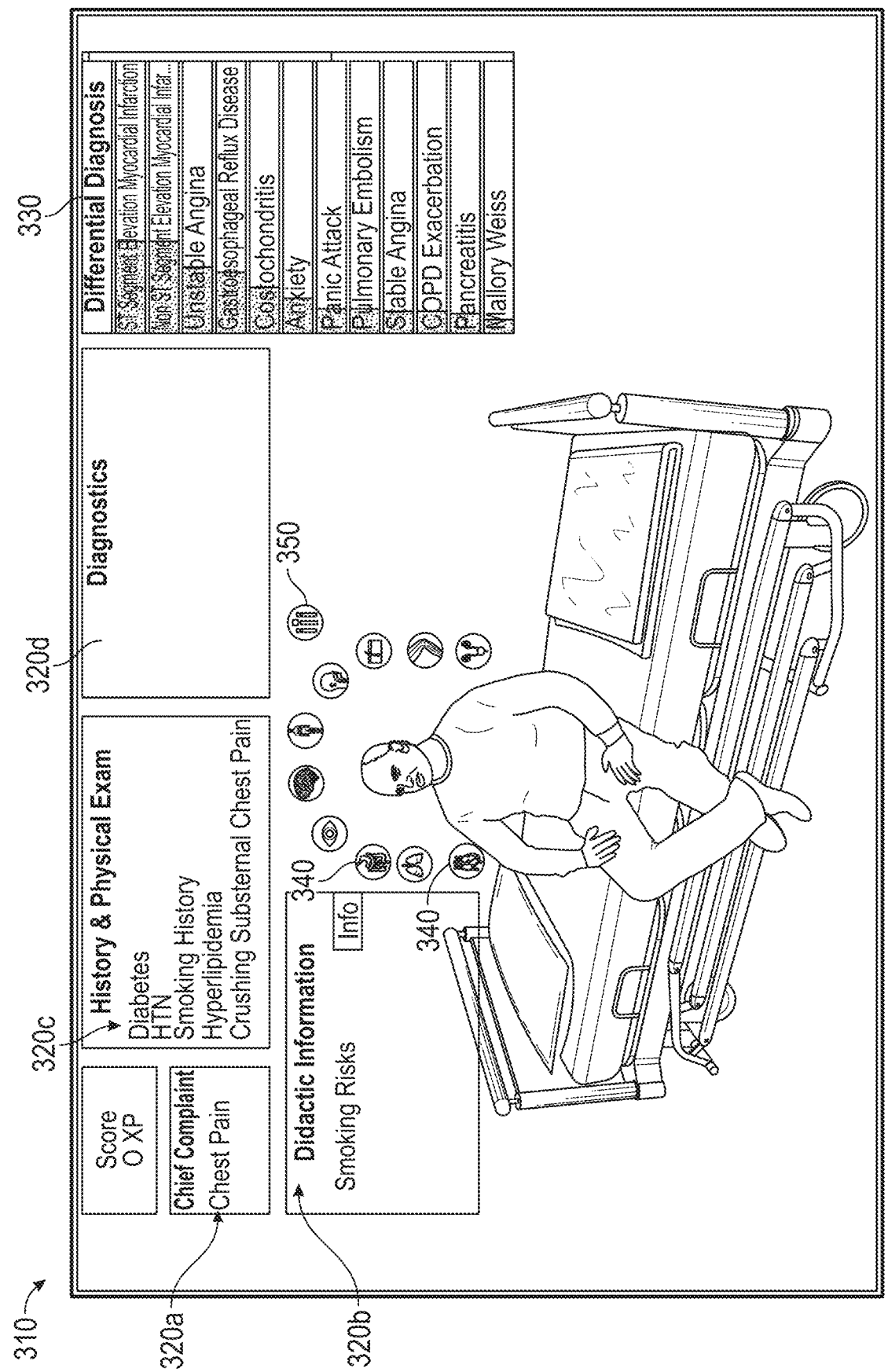

FIG. 3D provides an example of how application software 210 may update virtual reality environment 310 in response to the user selecting button 321 to commence the examination of the patient. During the examination, application software 210 may maintain a number of patient information overlays 320a-320d within virtual reality environment 310 in which patient information from the scenario data structure may be presented such as a chief complaint, other patient history, examination information (e.g., information that the user obtained by performing physical examinations on the patient in virtual reality environment 310), relevant didactic information, diagnostics information (e.g., results of diagnostics that the user may have ordered), etc. Application software 210 may populate some of the patient information in information overlays 320a-320d when the user commences the examination and may add more patient information as the user discovers it through examinations or diagnostic procedures.

Application software 210 may also generate a number of selectable components 340 that allow the user to physically examine the patient within virtual reality environment 310 to thereby obtain "examination information" from the patient information. For example, a cardiovascular component may allow the user to listen to a virtual heartbeat, an eye button may allow the user to view virtual images of the patient's eyes, a general exams/vitals button may allow the user to view the patient's vitals and other general state information, and other buttons may allow the user to view information about the current condition of the patient's other systems, structures, etc. All such examination information that is presented when the user selects selectable components 340 can be defined in and retrieved from the selected scenario data structure. As stated above, application software 210 may dynamically populate information overlays 320a-320d with such examination information as the user discovers it.

By reviewing the patient history and the examination information that the user obtains by performing the physical examinations available via selectable components 340, the user can determine which diagnostic procedures may provide further patient information that will be helpful in identifying the patient's condition(s). Accordingly, application software 210 may generate a diagnostics button 350 that allows the user to order diagnostic procedures for the patient.

Figure 3E:
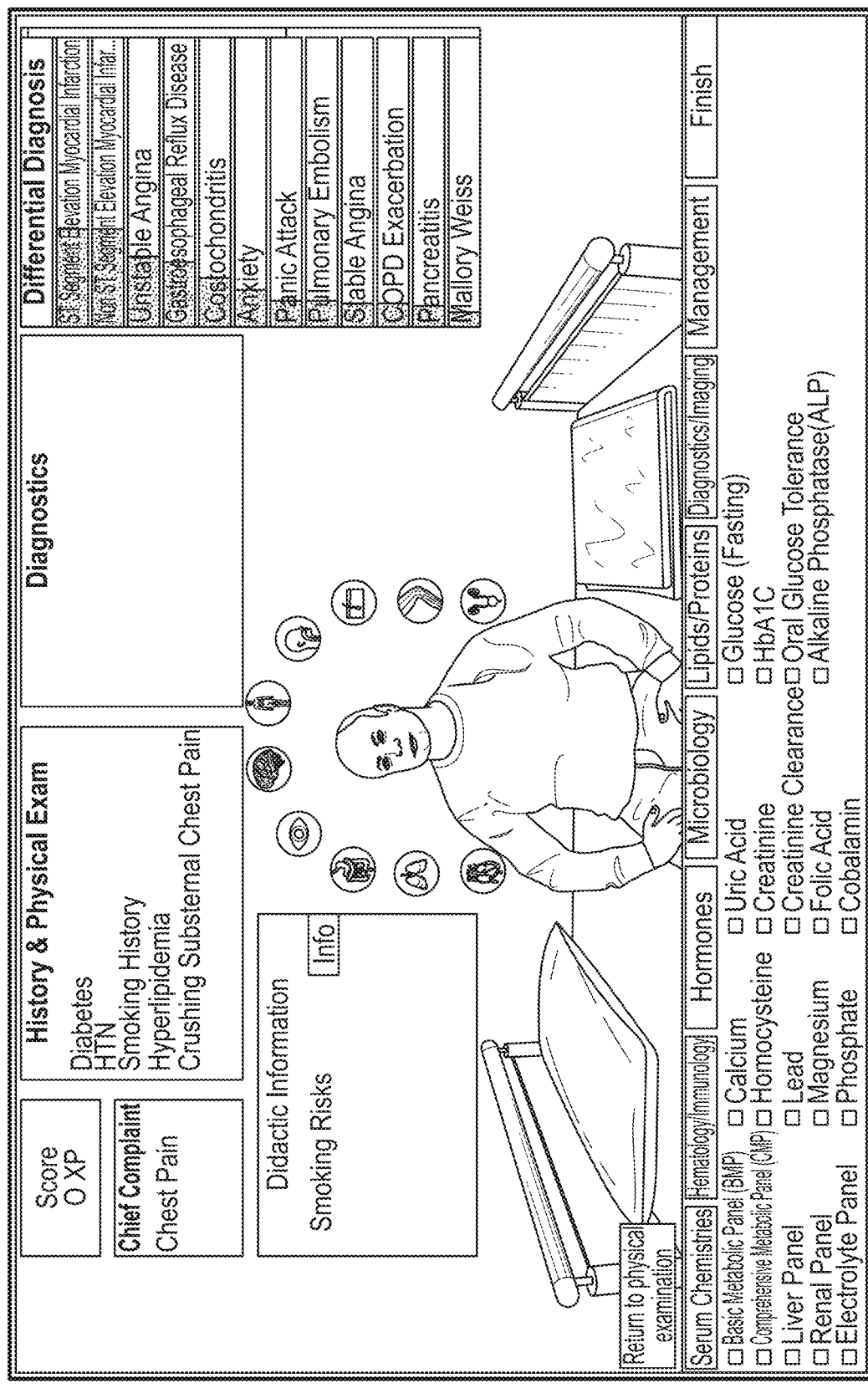

FIG. 3E provides an example of how application software 210 may update virtual reality environment 310 when the user selects diagnostics button 350 to include a diagnostics window 360 that lists all available diagnostic procedures. Notably, for any given scenario, it is likely that only a small subset of the available diagnostic procedures will be relevant to or helpful for diagnosing the condition that the scenario represents. Therefore, virtual reality environment 310 allows the user to use his or her judgment, based on any patient information the user has already obtained via virtual reality environment, to select appropriate diagnostic procedures to attempt to obtain the patient information that is most relevant to reaching the proper diagnosis.

Once the user selects a particular diagnostic procedure, application software 210 can obtain, from the patient information in the scenario data structure, the results of the particular diagnostic procedure (or "diagnostics information" of the patient information) and present them to the user (e.g., within a diagnostics result overlay (not shown)) and may populate the results of any correctly selected diagnostic procedure into information window 320d.

Accordingly, application software 210 creates virtual reality environment 310 to enable the user to retrieve patient information in a manner that resembles performing an examination of an actual patient. In some embodiments, as the user interacts with virtual reality environment 310, application software 210 may generate and update a score representing the extent to which the user is performing the proper examinations and ordering the proper diagnostics procedures to obtain the patient information that is most relevant to arriving at the correct diagnosis. Such scoring can encourage the user to repeat scenarios until mastering his or her diagnosing skills.

While performing an examination within virtual reality environment 310, at any time, the user may submit a diagnosis or otherwise request feedback. Application software 210 may generate such feedback based on the user's interactions to obtain the appropriate patient information (e.g., notifying the user that he or she failed to perform a particular examination or order a particular diagnostic procedure) and/or based on the submitted diagnosis. For example, FIG. 3F shows a feedback overlay 370 that application software 210 may generate. In some embodiments, application software 210 may present questions to probe the user's understanding and ensure that the user reached the proper diagnosis for the proper reasons.

Figure 4A:
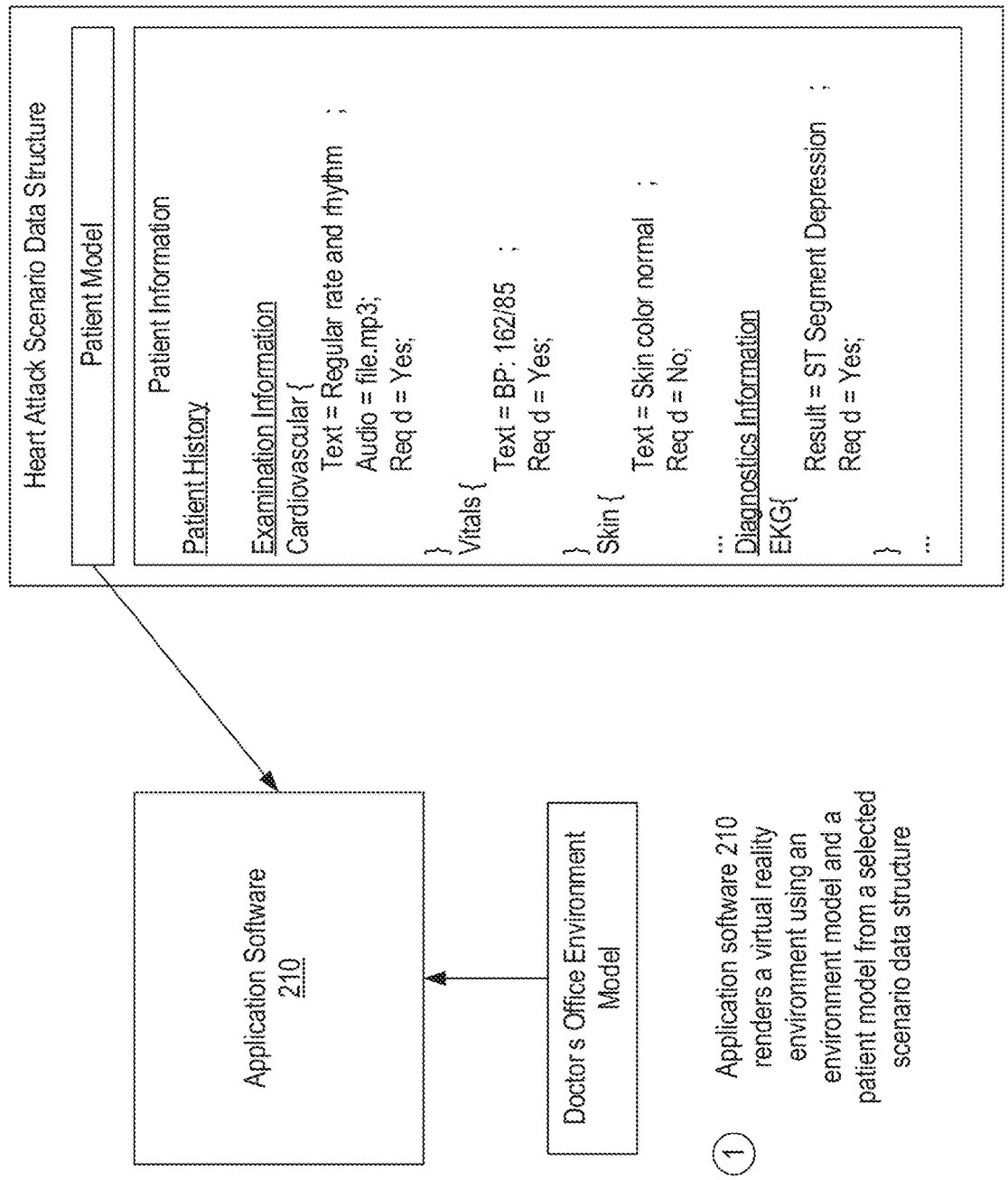
FIG. 4A-4D provide an example of how application software of the virtual reality platform may create a particular scenario in the virtual reality environment from a scenario data structure and how the application software can monitor the user's interactions with the virtual reality environment to provide feedback specific to the particular scenario.

FIGS. 4A-4D provide an example of how application software 210 can monitor the user's interaction within virtual reality environment 310 when a particular scenario is presented and generate feedback based on such interactions and the patient information of the underlying scenario data structure. In FIG. 4A, a simple example of a scenario data structure representing a heart attack scenario is provided. As shown, this heart attack scenario data structure can include various elements of patient information including elements of patient history, elements of examination information and elements of diagnostics information.

For each element of patient information, the scenario data structure may define textual, visual or audio content (e.g., the content that will be displayed to the user within virtual reality environment 310) as well as metadata defining whether (or the extent to which) the element is required/essential to reach the proper diagnosis for the proper reasons. For example, in the heart attack scenario, the scenario data structure may indicate that, to make the correct diagnosis for the proper reasons, it is required that the user examine the patient's vitals and cardiovascular system and order/perform an EKG. Although this example indicates that an element is either required or not required, in some embodiments, an element may be given a value from a range or set of values that defines its relative importance in diagnosing a condition that the scenario represents. For example, an essential element of the patient information may be given a value of 10 in a range from 0-10, while an irrelevant element of the patient information may be given a value of 0. Accordingly, virtual reality platform 200 may employ a variety of techniques to identify the relative importance of an examination or a diagnostic procedure in a given scenario. FIG. 4A also represents that, in step 1, application software 210 can render virtual reality environment 310 using the doctor's office environment model and the patient model.

Figure 4B:
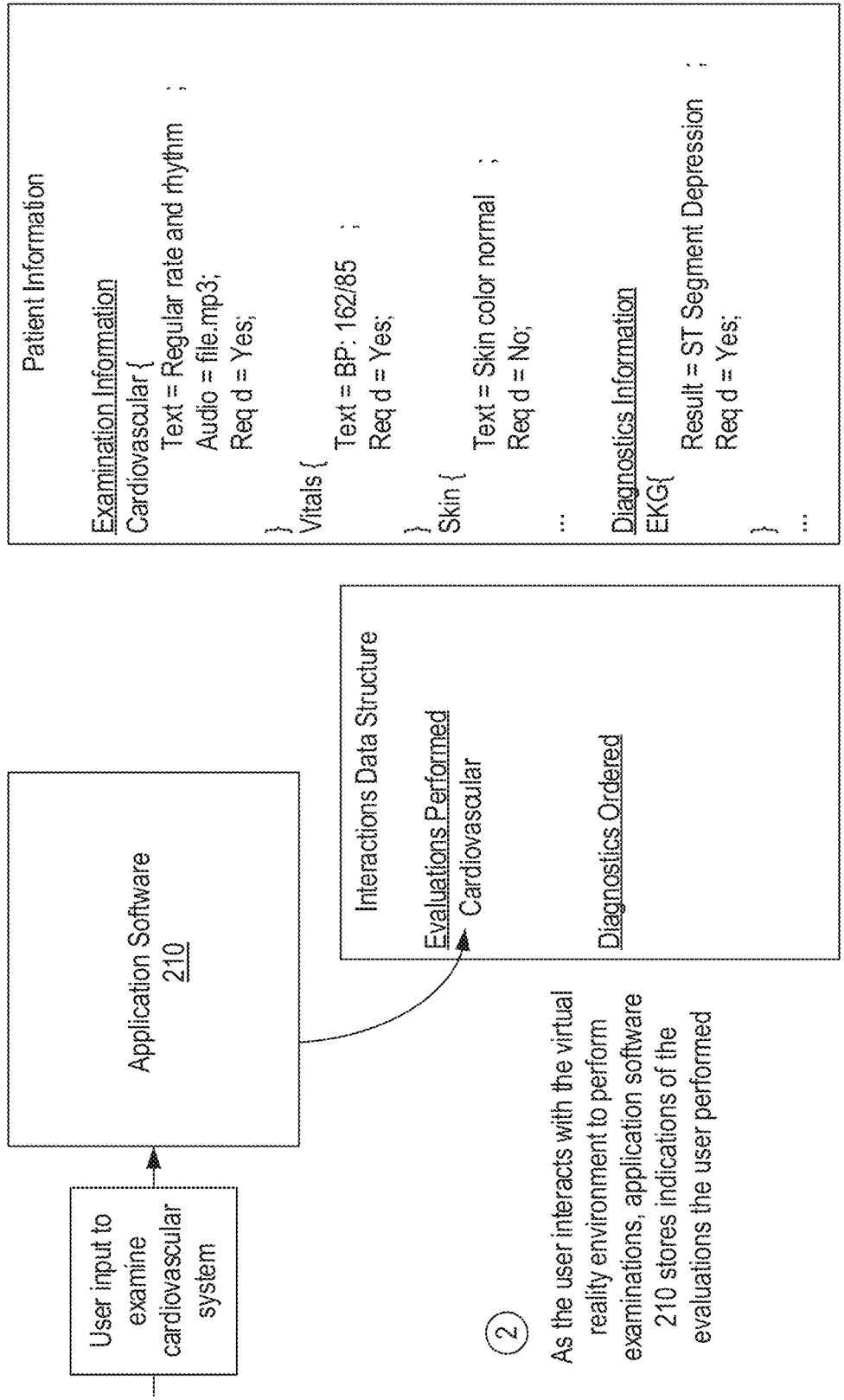

Turning to FIG. 4B, it is assumed that application software 210 has rendered virtual reality environment 310 and that the user has provided input to perform an examination of the patient's cardiovascular system (e.g., by selecting the appropriate selectable component 340). In addition to accessing the scenario data structure to retrieve the textual, visual and/or audio content of the selected element of the examination information and presenting such content to the user within virtual reality environment 310, in step 2, application software 210 can also store an indication that the user performed the cardiovascular examination (e.g., in an interactions data structure). In other words, application software 210 can store an indication that the user obtained the cardiovascular element of the examination information. Application software 210 can perform this functionality whenever the user performs an examination to retrieve a different element of the examination information for the particular scenario.

Figure 4C:
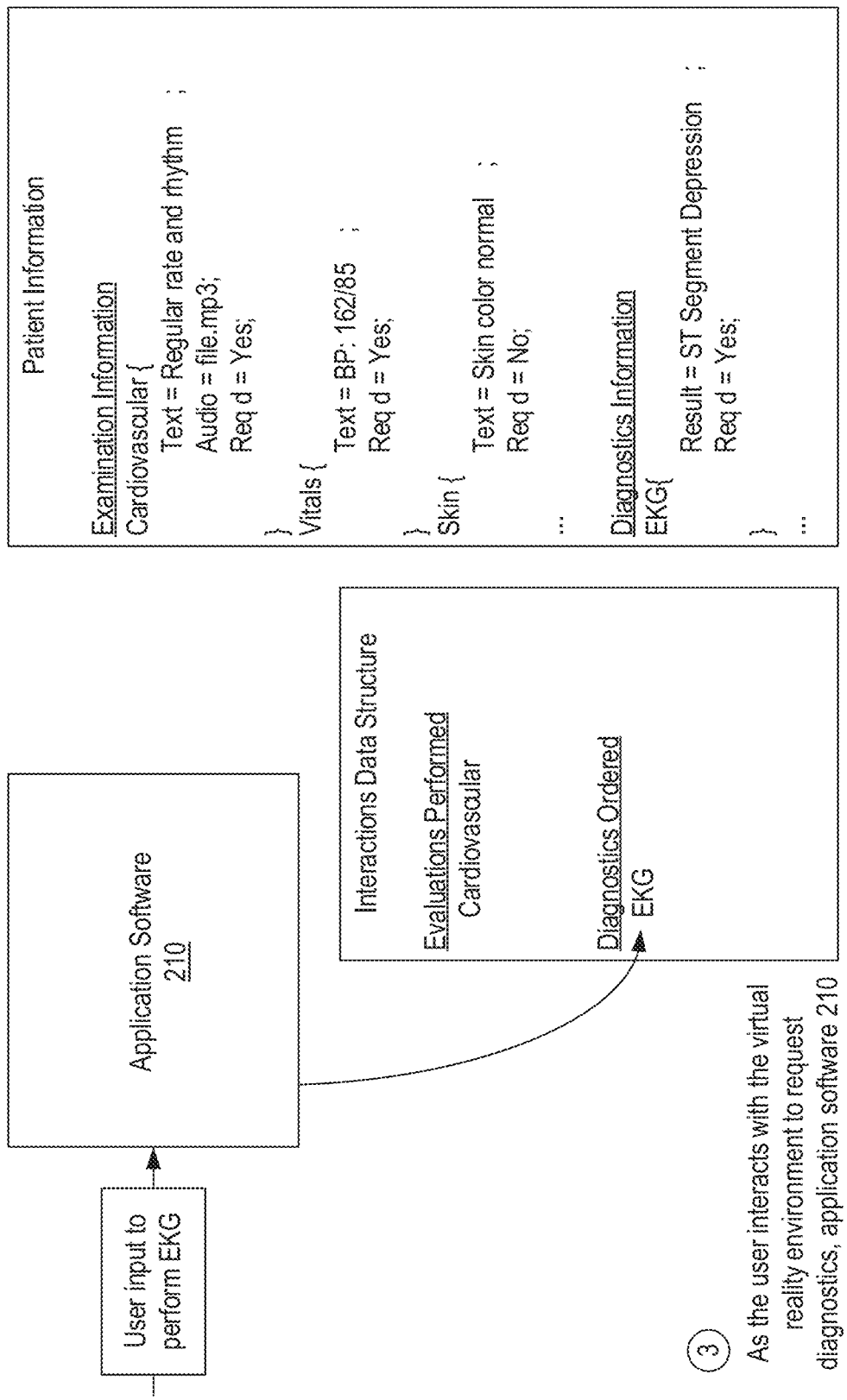

Turning to FIG. 4C, it is now assumed that the user has provided input to request an EKG (e.g., by selecting diagnostics button 350 and then selecting an EKG option in diagnostics window 360). In addition to accessing the scenario data structure to retrieve the results for the EKG from the EKG element of the diagnostics information and presenting the results to the user within virtual reality environment 310, in step 3, application software 210 can also store an indication that the user requested the EKG diagnostic procedure (e.g., in the interactions data structure). In other words, application software 210 can store an indication that the user obtained the EKG element of the diagnostics information. Application software 210 can perform this functionality whenever the user requests a diagnostics procedure to retrieve a different element of the diagnostics information for the particular scenario.

Figure 4D:
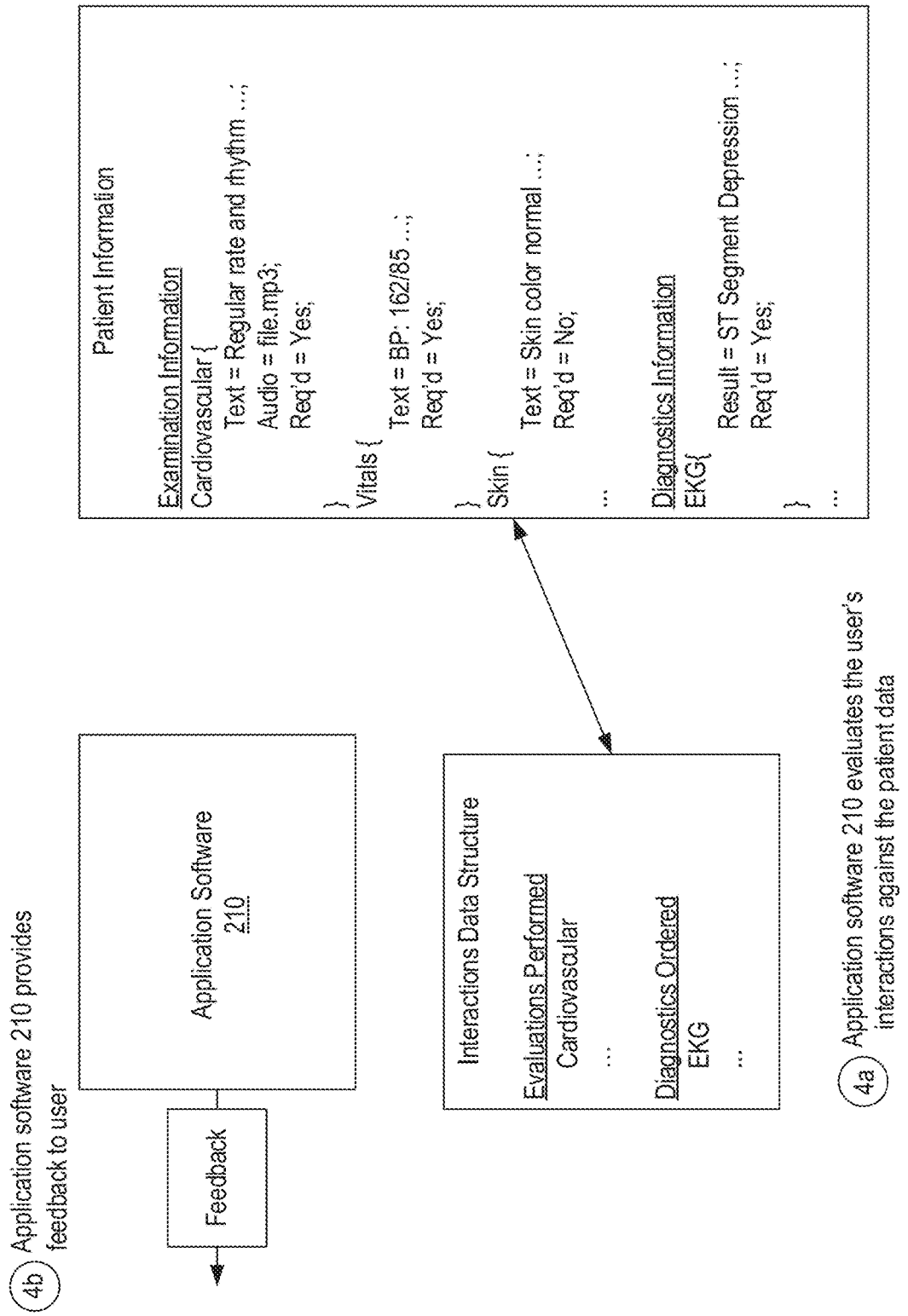

Turning to FIG. 4D, at any point during the user's examination (e.g., in response to each examination the user performs or each diagnostic procedure the user orders, in response to the user's request for feedback, in response to the user submitting a diagnosis, etc.), in step 4a, application software 210 can evaluate the user's interactions against the metadata in the scenario data structure. For example, application software 210 can determine whether the user performed each required/essential examination and ordered each required/essential diagnostic procedure. Then, in step 4b, application software 210 can provide appropriate feedback to the user (e.g., an adjustment to a score, an identification of an examination or diagnostic procedure that was missed, an explanation of why a submitted diagnosis was wrong, etc.). In this way, application software 210 can assist the user in learning which examinations and which diagnostic procedures should be performed given a certain set of patient information. In other words, virtual reality platform 200 not only allows the user to practice arriving at the correct diagnosis but enables the user to learn which elements of patient information should be considered to arrive at the correct diagnosis for the correct reasons.

Figure 5:
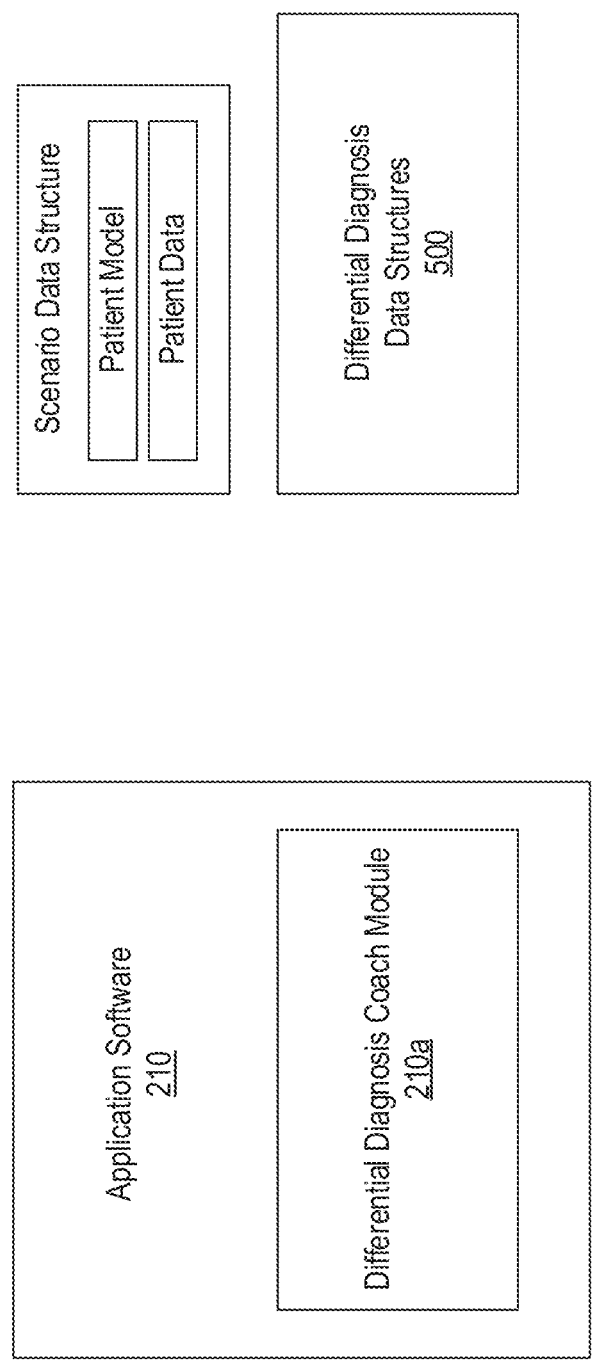
FIG. 5 illustrates how the application software of the virtual reality platform may include a differential diagnosis coach module that uses differential diagnosis data structures to train a user in performing differential diagnosis in a virtual reality environment.

In some embodiments as represented in FIG. 5, application software 210 may include differential diagnosis coach module 210a to enable application software 210 to provide a differential diagnosis coach feature. The term differential diagnosis refers to the process of differentiating between two or more conditions which share similar signs or symptoms. For example, when a patient is experiencing chest pain, the underlying condition could be many things ranging from anxiety to a heart attack. Differential diagnosis coach module 210a can assist medical personnel in developing their differential diagnosis skills.

As an overview, differential diagnosis coach module 210a can leverage differential diagnosis data structures 500 to provide real-time feedback as the user interacts with virtual reality environment 310 to attempt to diagnose the condition that the scenario represents. More particularly, differential diagnosis coach module 210a can use differential diagnosis data structures 500 to calculate and adjust a ranking or likelihood of conditions (or potential diagnoses) based on the user's interaction with virtual reality environment 310. Based on such likelihoods, differential diagnosis coach module 210a can populate and adjust the conditions within list 331 of differential diagnosis coach overlay 330. In this way, virtual reality platform 200 can assist the user in recognizing the importance of the examinations and diagnostic procedures he or she may perform when attempting to diagnose the condition that a particular scenario represents.

FIG. 6 provides a simple example of the content that differential diagnosis data structures 500 may contain to enable differential diagnosis coach module 210a to provide real-time feedback via differential diagnosis coach overlay 330. Some of differential diagnosis data structures 500 may be maintained in database 240 and retrieved by application software 210, while others may be dynamically created and/or updated by application software 210 as the user interacts with virtual reality environment 310. In some embodiments, a unique set of differential diagnosis data structures 500 may be associated with each scenario data structure.

As shown, differential diagnosis data structures 500 can include a prevalence/incidence data structure(s) 501 which map a prevalence/incidence value(s) to each condition that may be available in a particular scenario. For example, in FIG. 6, prevalence/incidence data structure 501 shows three conditions that are each associated with prevalence/incidence value of 1%. For simplicity, prevalence and incidence are combined in this example, but differential diagnosis data structures 500 could define a prevalence value and a separate incidence value for each condition. Of importance is that such prevalence/incidence value(s) can be used as a starting point for calculating a likelihood of the condition. If prevalence or incidence data is not available for a condition, the likelihood may be assigned based on expert physician opinion.

Differential diagnosis data structures 500 may also include a diagnosis likelihood data structure(s) 502 in which differential diagnosis coach module 210a may maintain a likelihood value for each condition where the likelihood value is dynamically adjusted as the user discovers elements of the patient information through his or her interactions with virtual reality environment 310. In FIG. 6, the likelihood values are each 1% which may be the case before the user has commenced examining the patient. In other words, the likelihood values may be initially set based on the prevalence/incidence value(s) for the condition.

Differential diagnosis data structures 500 may also include a likelihood ratio data structure 503 which associates each condition with a likelihood ratio for each element of the patient information. In some embodiments, these likelihood ratios can be derived from a variety of medical statistics such as sensitivity, specificity, odds ratios, post-test probability, relative risk, etc. In some embodiments, these likelihood ratios may also or alternatively be defined by expert physician opinion. Notably, each element of patient information may be associated with a different likelihood ratio for each possible condition/diagnosis.

FIG. 6 provides a simple example in which the condition ST Segment Elevation Myocardial Infarction is associated with a likelihood ratio of 1.2 for element 1 of the patient information, a likelihood ratio of 2 for element 2 of the patient information, a likelihood ratio of 0.8 for element 3 of the patient information and a likelihood ratio of 1 for element 4 of the patient information. In this example, a likelihood ratio of 1 can indicate that the element does not impact the likelihood that the patient has the condition. A likelihood ratio greater than 1 can indicate that the element increases the likelihood that the patient has the condition. A likelihood ratio less than 1 can indicate that the element decreases the likelihood that the patient has the condition. As a particular example, element 1 could be an element of the patient history such as chest pain and element 2 could be an element of the diagnostics information such as the results of an EKG. On the other hand, element 3 could represent any element of the patient information that would suggest that the patient may not have an ST Segment Elevation Myocardial Infarction and element 4 could represent any element that is irrelevant to diagnosing an ST Segment Elevation Myocardial Infarction.

In some embodiments, the likelihood ratios may not only be associated with particular elements of the patient information, but with particular values of such elements. For example, one likelihood ratio may be defined for a first range of heart rates and another likelihood ratio may be defined for a second range of heart rates. Accordingly, likelihood ratios can be associated with elements at different levels of granularity.

Differential diagnosis coach module 210a can be configured to monitor the user's interactions with virtual reality environment 310 and, based on such interactions, dynamically adjust the likelihood values in diagnosis likelihood data structure 502 using likelihood ratio data structure 503. Differential diagnosis coach module 210a can then use the dynamically adjusted likelihood values to update differential diagnosis coach overlay 330 accordingly. FIGS. 7A-7D provide an example of how differential diagnosis coach module 210a may perform such functionality.

Figure 7A:
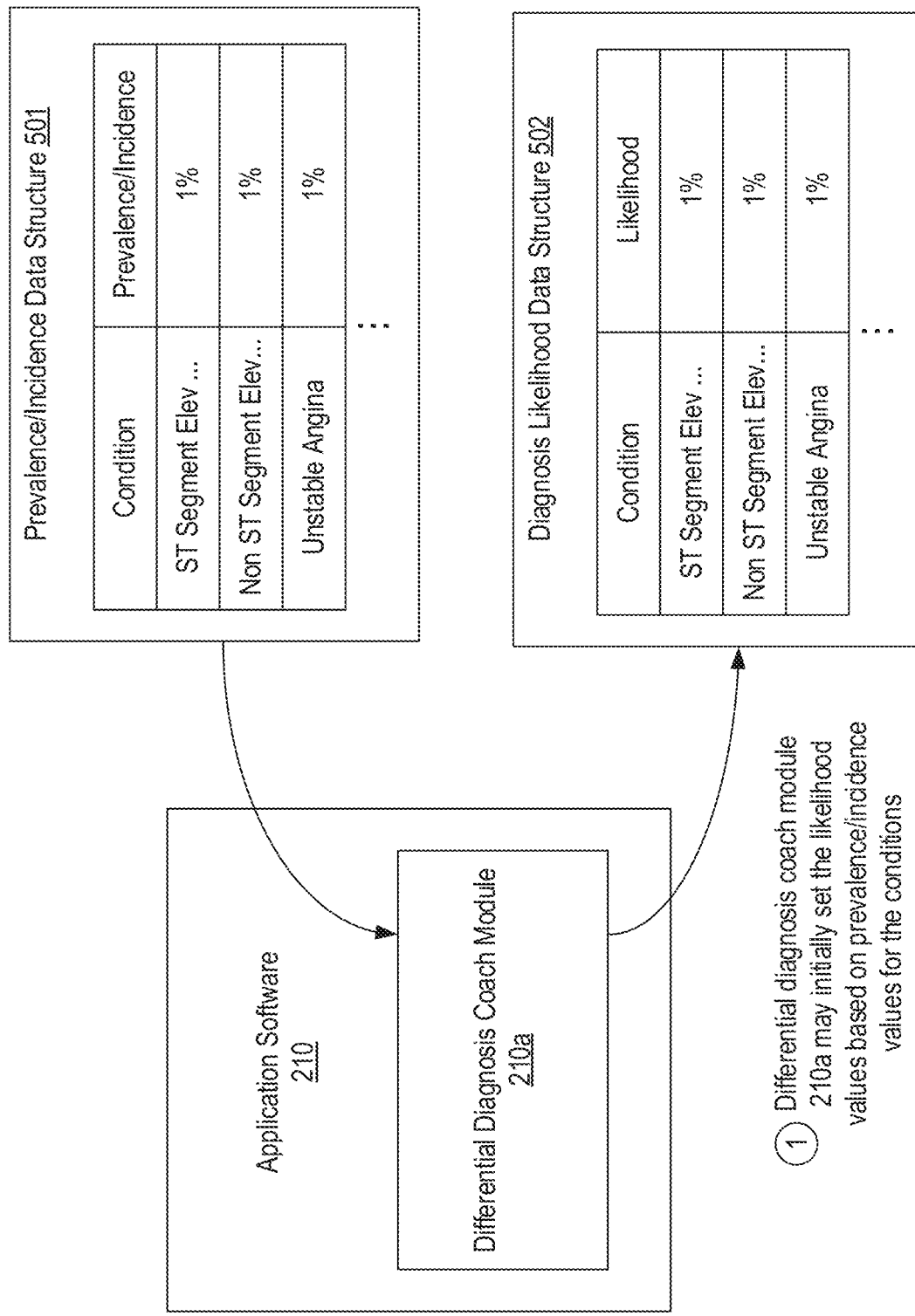
FIGS. 7A-7D provide an example of how the differential diagnosis coach module of the application software can implement a differential diagnosis coach feature when a particular scenario is represented in the virtual reality environment.

Turning to FIG. 7A, as part of loading a scenario and in step 1, differential diagnosis coach module 210a may employ the prevalence/incidence values from prevalence/incidence data structure 501 to initially set the likelihood values in diagnosis likelihood data structure 502. Although not shown, differential diagnosis coach module 210a (or application software 210) could then populate differential diagnostics coach overlay 330 based on the initially set likelihood values. Accordingly, the conditions in list 331 could be initially ordered based on prevalence and/or incidence or other information that is not specific to the patient information for the particular scenario.

Figure 7B:
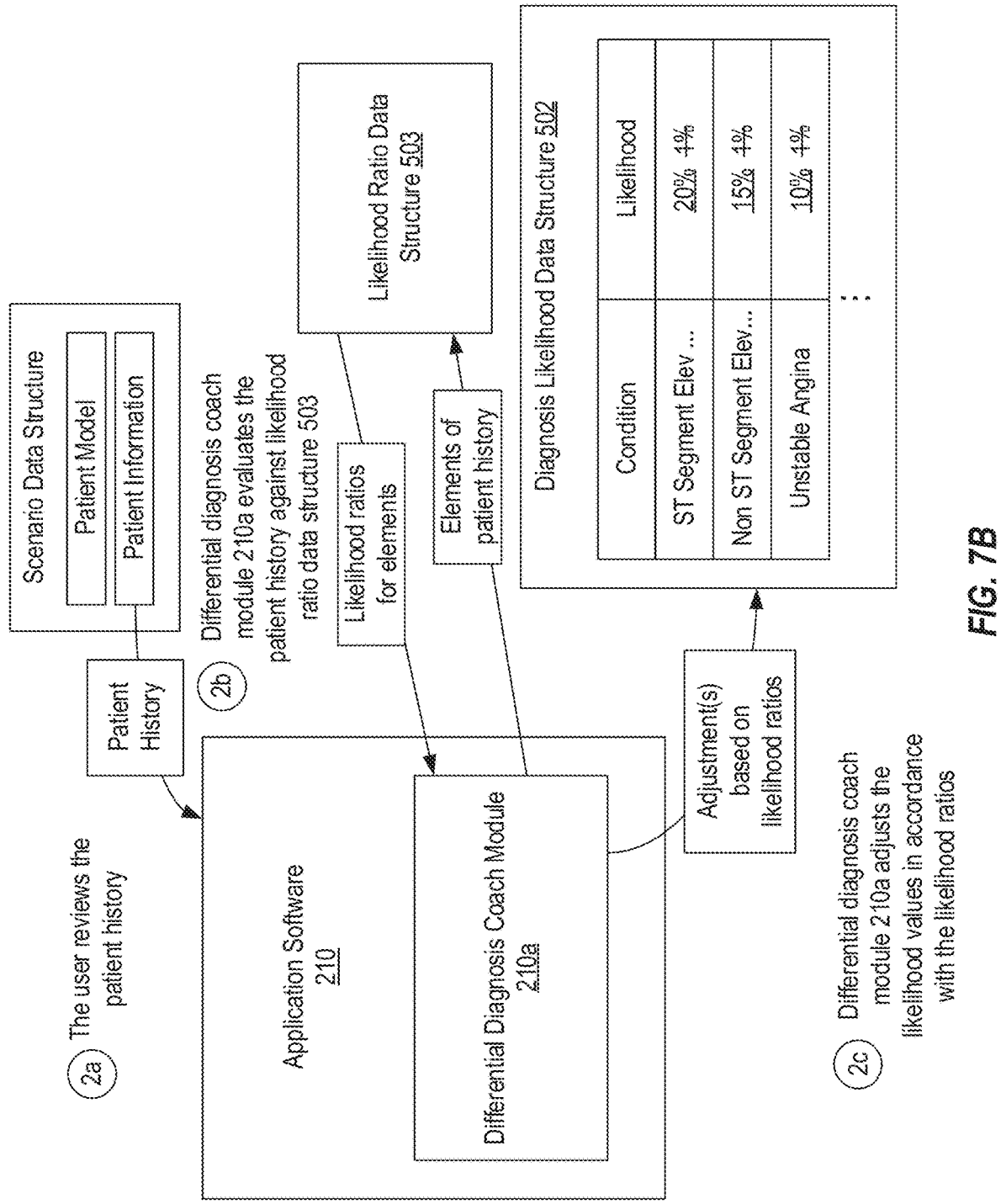

Turning to FIG. 7B, in step 2a, it is assumed that the user has selected to review the patient history. For example, step 2a could represent the user's selection of selectable component 313. As part of step 2a, application software 210 could retrieve the patient history of the patient information defined in the scenario data structure and present it in history overlay 320 in virtual reality environment 310. In step 2b, and in response to the user having selected to review the patient history, differential diagnosis coach module 210a may evaluate the elements of patient history against likelihood ratio data structure 503 to thereby obtain the likelihood ratios for any elements that are present in the patient history that the user has reviewed. As a simple example, if the patient history includes an element that indicates that the patient is experiencing chest pain (or a particular level of chest pain), differential diagnosis coach module 210a could retrieve a likelihood ratio associated with a chest pain element (or a chest pain element with a matching value or range of values) for each possible condition/diagnosis. Having received the likelihood ratios, in step 2c, differential diagnosis coach module 210a can apply the likelihood ratios to the corresponding likelihood values in diagnosis likelihood data structure 502 to thereby adjust the likelihood values.

Again using the chest pain example and assuming for simplicity that likelihood ratios for no other elements were applied in step 2c, FIG. 7B would represent a scenario where the likelihood ratio for a chest pain element associated with the ST Segment Elevation Myocardial Infarction condition caused the likelihood value for the ST Segment Elevation Myocardial Infarction condition to be increased from 1% to 20%. Although not shown, in conjunction with step 2c, differential diagnosis coach module 210a (or application software 210) could update differential diagnostics coach overlay 330 based on the updated likelihood values (e.g., by reordering the conditions based on their updated likelihood values). In this way, differential diagnosis coach module 210a can present the user with the most likely diagnoses based on the elements of the patient information that the user has reviewed.

Figure 7C:
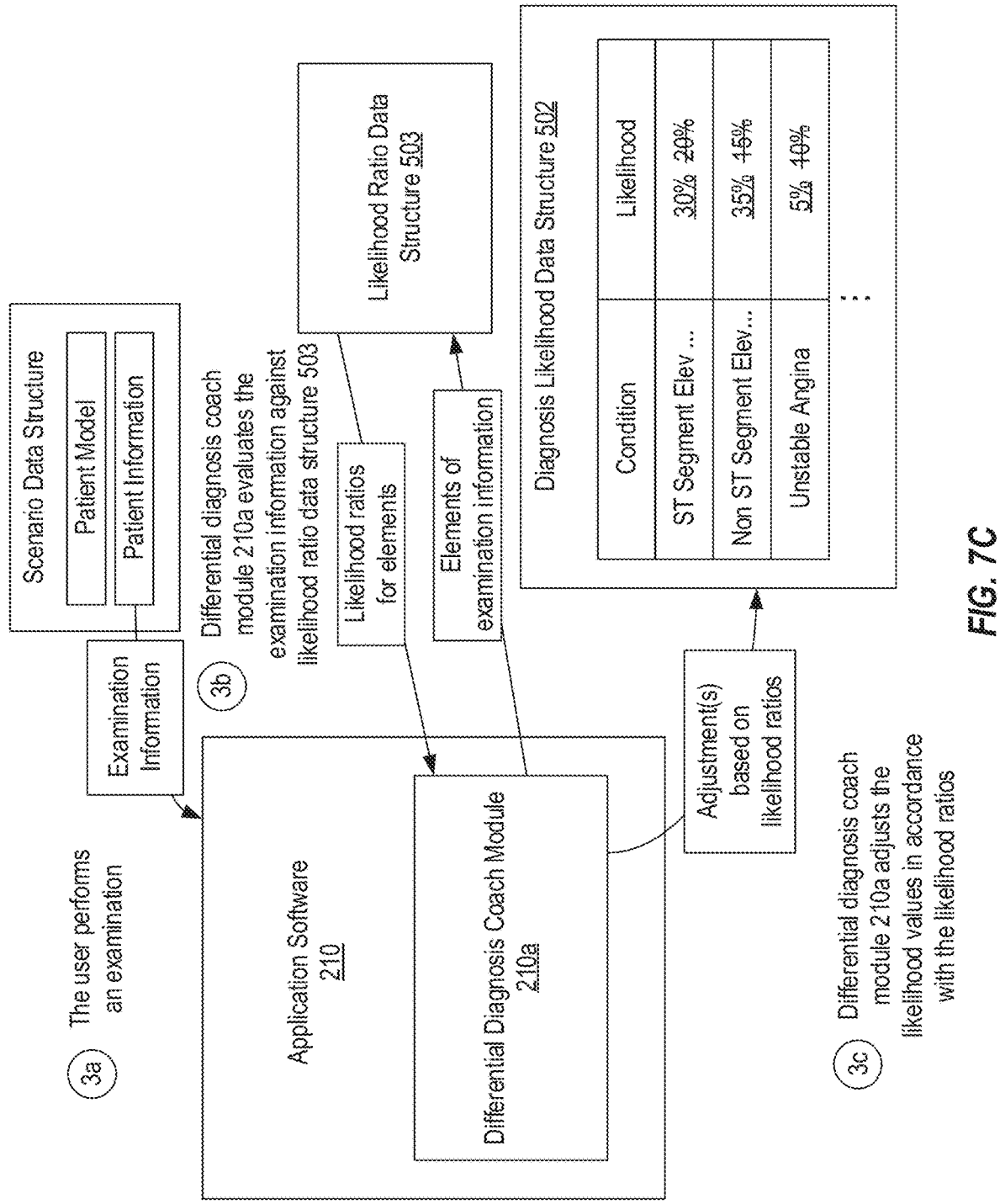

FIG. 7C is substantially similar to FIG. 7B but represents a scenario where the user has performed an examination to obtain elements of examination information from the patient information of the scenario data structure. For example, in step 3a, the user may select any of selectable components 340 to review elements of the examination information for the particular scenario. In response, in step 3b, differential diagnosis coach module 210a can evaluate the elements of examination information that the user has reviewed/obtained against likelihood ratio data structure 503 to obtain the likelihood ratios for such elements for the possible conditions. Then, in step 3c, differential diagnosis coach module 210a can apply the likelihood ratios to the corresponding likelihood values in diagnosis likelihood data structure 502 to thereby adjust the likelihood values. Notably, these steps may be performed each time the user performs an examination and obtains additional elements of examination information. Although not shown, in conjunction with step 3c, differential diagnosis coach module 210a (or application software 210) could update differential diagnostics coach overlay 330 based on the updated likelihood values (e.g., by reordering the conditions based on their updated likelihood values). In this way, differential diagnosis coach module 210a can inform the user how the examination he or she performed, or more particularly, how the examination information obtained through the examination, impacts the likelihood of the potential diagnoses.

Figure 7D:
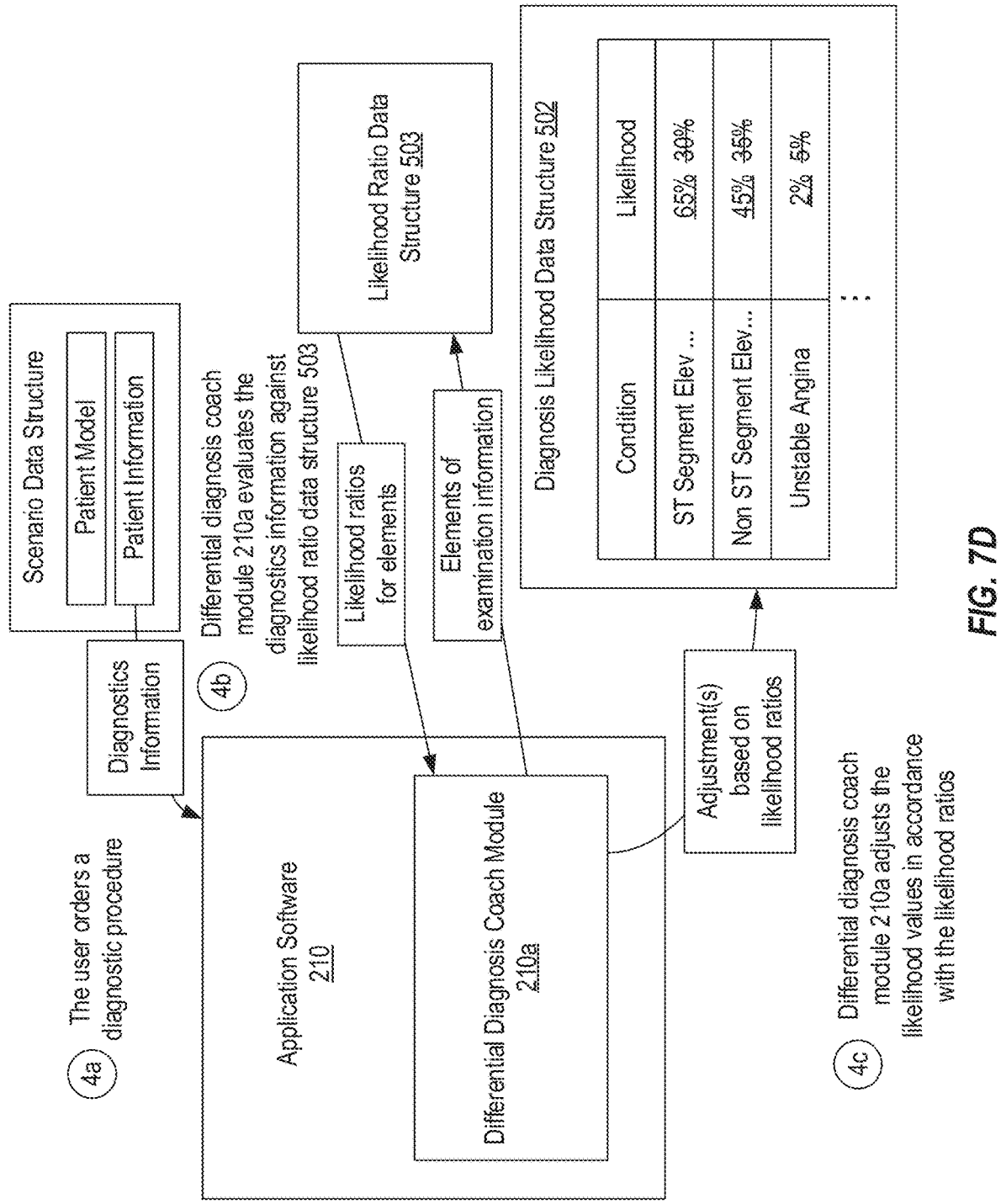

FIG. 7D is also substantially similar to FIG. 7B but represents a scenario where the user has ordered a diagnostic procedure to obtain diagnostics information from the patient information of the scenario data structure. For example, in step 4a, the user may select any of available diagnostic procedures in diagnostic procedure window 360 to review elements of the diagnostics information for the particular scenario. In response, in step 3b, differential diagnosis coach module 210a can evaluate the elements of diagnostics information that the user has reviewed/obtained against likelihood ratio data structure 503 to obtain the likelihood ratios for such elements for the possible conditions. Then, in step 3c, differential diagnosis coach module 210a can apply the likelihood ratios to the corresponding likelihood values in diagnosis likelihood data structure 502 to thereby adjust the likelihood values. Notably, these steps may be performed each time the user requests a diagnostic procedure. Although not shown, in conjunction with step 4c, differential diagnosis coach module 210a (or application software 210) could update differential diagnostics coach overlay 330 based on the updated likelihood values (e.g., by reordering the conditions based on their updated likelihood values). In this way, differential diagnosis coach module 210a can inform the user how the results of the diagnostic procedure he or she ordered impact the likelihood of the potential diagnoses.

By implementing the process depicted in FIGS. 7A-7D, differential diagnosis coach module 210a can train the user to correctly perform differential diagnosis. For example, as the user discovers increasingly more elements of patient information, differential diagnosis coach module 210a can assist the user to learn which additional elements of patient information he or she should pursue to arrive at the correct diagnosis as well as which additional elements of patient information will not be helpful in distinguishing between multiple possible diagnoses.

Differential diagnosis coach module 210a may employ a variety of algorithms to generate and adjust the likelihood values in diagnosis likelihood data structure 502 based on the likelihood ratios of the elements of patient information the user has discovered. As a simple example, differential diagnosis coach module 210a could multiply the current likelihood value for a particular condition by the likelihood ratio of any discovered element of patient information that is associated with the particular condition. In this way, the current likelihood value, which would be based on the likelihood ratios associated with any elements of patient information the user has already discovered, would be scaled by the likelihood ratios of any newly discovered elements of patient information.

In summary, a virtual reality platform in accordance with embodiments of the present invention can be configured to enable a user to use his or her computing device to train in diagnosing virtual patients. The virtual reality platform can therefore enable such users to much more quickly obtain the necessary experience to diagnose actual patients with a high level of success. The unique configuration of the virtual reality platform's application software and the unique data structures it employs also enable the user to train in performing differential diagnosis.

Embodiments of the present invention may comprise or utilize special purpose or general-purpose computers including computer hardware, such as, for example, one or more processors and system memory. Embodiments within the scope of the present invention also include physical and other computer-readable media for carrying or storing computer-executable instructions and/or data structures. Such computer-readable media can be any available media that can be accessed by a general purpose or special purpose computer system.

Computer-readable media are categorized into two disjoint categories: computer storage media and transmission media. Computer storage media (devices) include RAM, ROM, EEPROM, CD-ROM, solid state drives ("SSDs") (e.g., based on RAM), Flash memory, phase-change memory ("PCM"), other types of memory, other optical disk storage, magnetic disk storage or other magnetic storage devices, or any other similar storage medium which can be used to store desired program code means in the form of computer-executable instructions or data structures and which can be accessed by a general purpose or special purpose computer. Transmission media include signals and carrier waves. Because computer storage media and transmission media are disjoint categories, computer storage media does not include signals or carrier waves.

Computer-executable instructions comprise, for example, instructions and data which, when executed by a processor, cause a general-purpose computer, special purpose computer, or special purpose processing device to perform a certain function or group of functions. The computer executable instructions may be, for example, binaries, intermediate format instructions such as assembly language or P-Code, or even source code.

Those skilled in the art will appreciate that the invention may be practiced in network computing environments with many types of computer system configurations, including, personal computers, desktop computers, laptop computers, message processors, hand-held devices, multi-processor systems, microprocessor-based or programmable consumer electronics, network PCs, minicomputers, mainframe computers, mobile telephones, PDAs, tablets, smart watches, pagers, routers, switches, and the like.

The invention may also be practiced in distributed system environments where local and remote computer systems, which are linked (either by hardwired data links, wireless data links, or by a combination of hardwired and wireless data links) through a network, both perform tasks. In a distributed system environment, program modules may be located in both local and remote memory storage devices. An example of a distributed system environment is a cloud of networked servers or server resources. Accordingly, the present invention can be hosted in a cloud environment.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description.

What is claimed:

1. A method, implemented by a virtual reality platform that includes application software, for providing a virtual reality environment for training medical personnel to diagnose patients, the method comprising:
   generating, by the application software of the virtual reality platform, a virtual reality environment that includes a patient, the patient being associated with patient information that represents a first condition that the patient has out of a plurality of possible conditions;
   presenting a differential diagnosis coach overlay within the virtual reality environment, the differential diagnosis coach overlay identifying a first plurality of conditions of the plurality of possible conditions and a likelihood value for each of the first plurality of conditions;
   detecting a first user interaction with the virtual reality environment, the first user interaction identifying a first examination or diagnostics procedure that a user desires to perform on the patient in the virtual reality environment;
   in response to detecting the first user interaction, accessing the patient information to retrieve one or more elements of the patient information that correspond with the first examination or diagnostics procedure;
   presenting, in the virtual reality environment, the one or more elements of the patient information that correspond with the first examination or diagnostics procedure; and
   in conjunction with presenting the one or more elements of the patient information that correspond with the first examination or diagnostics procedure, adjusting a score that is based on which elements of the patient information the user has discovered by interacting with the virtual reality environment.

2. The method of claim 1, wherein the patient information includes patient history, examination information and diagnostics information.

3. The method of claim 2, further comprising:
   prior to detecting the first user interaction, retrieving and presenting, in the virtual reality environment, the patient history.

4. The method of claim 2, wherein the first user interaction identifies a first examination that the user desires to perform on the patient in the virtual reality environment, and wherein the one or more elements of the patient information comprise one or more elements of the examination information.

5. The method of claim 2, wherein the first user interaction identifies a first diagnostics procedure that the user desires to perform on the patient in the virtual reality environment, and wherein the one or more elements of the patient information comprise one or more elements of the diagnostics information.

6. The method of claim 1, further comprising:
   determining that the one or more elements of the patient information that correspond with the first examination or diagnostics procedure are identified as essential to diagnosing the first condition; and
   wherein adjusting the score comprises increasing the score.

7. The method of claim 1, further comprising:
   determining that the one or more elements of the patient information that correspond with the first examination or diagnostics procedure are identified as not relevant to diagnosing the first condition; and
   wherein adjusting the score comprises decreasing the score.

8. The method of claim 1, further comprising:
- detecting a second user interaction with the virtual reality environment, the second user interaction identifying a second examination or diagnostics procedure that the user desires to perform on the patient in the virtual reality environment;
- in response to detecting the second user interaction, accessing the patient information to retrieve one or more elements of the patient information that correspond with the second examination or diagnostics procedure;
- presenting, in the virtual reality environment, the one or more elements of the patient information that correspond with the second examination or diagnostics procedure; and
- in conjunction with presenting the one or more elements of the patient information that correspond with the second examination or diagnostics procedure, adjusting a score that is based on which elements of the patient information the user has discovered by interacting with the virtual reality environment such that the score is adjusted based on the discovery of the one or more elements of patient information that correspond with the first examination or diagnostics procedure and on the discovery of the one or more elements of patient information that correspond with the second examination or diagnostics procedure.

9. The method of claim 1, further comprising:
- detecting user interaction that indicates the user's desire to receive feedback;
- determining one or more elements of the patient information that the user failed to discover through interactions with the virtual reality environment; and
- presenting to the user the one or more elements of the patient information that the user failed to discover.

10. The method of claim 9, wherein presenting to the user the one or more elements of the patient information that the user failed to discover comprises presenting to the user an identification of an examination or a diagnostics procedure that the user failed to perform.

11. The method of claim 1, wherein presenting, in the virtual reality environment, the one or more elements of the patient information that correspond with the first examination or diagnostics procedure comprises presenting one or more of textual content, visual content or audio content.

12. The method of claim 1, further comprising:
- in conjunction with accessing the patient information to retrieve the one or more elements of the patient information that correspond with the first examination or diagnostics procedure, adjusting the likelihood value for at least one of the first plurality of conditions.

13. The method of claim 12, wherein adjusting the likelihood value for at least one of the first plurality of conditions comprises:
- for each of the at least one of the first plurality of conditions:
  - identifying, for each of the one or more elements, a likelihood ratio associated with the condition; and
  - applying each identified likelihood ratio to the likelihood value for the condition.

14. The method of claim 13, further comprising:
- after adjusting the likelihood value for at least one of the first plurality of conditions, reordering the first plurality of conditions that are identified in the differential diagnosis coach overlay.

15. The method of claim 1, wherein the first plurality of conditions is less than all of the plurality of possible conditions.

16. One or more computer storage media storing computer executable instructions which when executed implement application software of a virtual reality platform, wherein the application software is configured to perform a method for providing a virtual reality environment for training medical personnel to diagnose patients, the method comprising:
- generating a virtual reality environment that includes a patient, the patient being associated with patient information that represents a first condition that the patient has out of a plurality of possible conditions;
- presenting a differential diagnosis coach overlay in the virtual reality environment, the differential diagnosis coach overlay identifying a first plurality of conditions of the plurality of possible conditions and a likelihood value for each of the first plurality of conditions detecting a first user interaction with the virtual reality environment, the first user interaction identifying a first examination or diagnostics procedure that a user desires to perform on the patient in the virtual reality environment;
- in response to detecting the first user interaction, accessing the patient information to retrieve one or more elements of the patient information that correspond with the first examination or diagnostics procedure;
- in conjunction with accessing the patient information to retrieve the one or more elements of the patient information that correspond with the first examination or diagnostics procedure, adjusting the likelihood value for at least one of the first plurality of conditions; and
- after adjusting the likelihood value for at least one of the first plurality of conditions, adjusting the first plurality of conditions that are identified in the differential diagnosis coach overlay.

17. The computer storage media of claim 16, wherein adjusting the likelihood value for at least one of the first plurality of conditions comprises:
- for each of the at least one of the first plurality of conditions:
  - identifying, for each of the one or more elements, a likelihood ratio associated with the condition; and
  - applying each identified likelihood ratio to the likelihood value for the condition.

18. The computer storage media of claim 16, further comprising:
- detecting a second user interaction with the virtual reality environment, the second user interaction identifying a second examination or diagnostics procedure that the user desires to perform on the patient in the virtual reality environment;
- in response to detecting the second user interaction, accessing the patient information to retrieve one or more elements of the patient information that correspond with the second examination or diagnostics procedure;
- in conjunction with accessing the patient information to retrieve the one or more elements of the patient information that correspond with the second examination or diagnostics procedure, adjusting the likelihood value for at least one of the first plurality of conditions; and
- after adjusting the likelihood value for at least one of the first plurality of conditions, adjusting the first plurality of conditions that are identified in the differential diagnosis coach overlay.

19. A method, implemented by a virtual reality platform that includes application software, for providing a virtual reality environment for training medical personnel to diagnose patients, the method comprising:

generating, by the application software of the virtual reality platform, a virtual reality environment that includes a patient, the patient being associated with patient information that represents a first condition that the patient has out of a plurality of possible conditions;

detecting a first user interaction with the virtual reality environment, the first user interaction identifying a first examination that a user desires to perform on the patient in the virtual reality environment;

in response to detecting the first user interaction, accessing the patient information to retrieve one or more elements of examination information that correspond with the first examination;

presenting, in the virtual reality environment, the one or more elements of the examination information that correspond with the first examination;

detecting a second user interaction with the virtual reality environment, the second user interaction identifying a first diagnostics procedure that the user desires to perform on the patient in the virtual reality environment;

in response to detecting the second user interaction, accessing the patient information to retrieve one or more elements of diagnostics information that correspond with the first diagnostics procedure;

presenting, in the virtual reality environment, the one or more elements of the diagnostics information that correspond with the first diagnostics procedure; and maintaining a differential diagnostics coach overlay within the virtual reality environment, the differential diagnosis coach overlay identifying a first plurality of conditions of the plurality of possible conditions and a likelihood value for each of the first plurality of conditions, wherein maintaining the different diagnostics coach overlay includes adjusting the likelihood values for at least some of the first plurality of conditions in response to presenting the one or more elements of the examination information and the one or more elements of diagnostics information.

* * * * *